US012606589B2

(12) United States Patent
Obika et al.

(10) Patent No.: US 12,606,589 B2
(45) Date of Patent: Apr. 21, 2026

(54) BRIDGED NUCLEOSIDE AND NUCLEOTIDE USING SAME

(71) Applicants: Osaka University, Osaka (JP); Japan as Represented by Director General of National Institute of Health Sciences, Kawasaki (JP)

(72) Inventors: Satoshi Obika, Osaka (JP); Takao Yamaguchi, Osaka (JP); Hibiki Komine, Osaka (JP); Takaya Sugiura, Osaka (JP); Takao Inoue, Kawasaki (JP); Tokuyuki Yoshida, Kawasaki (JP)

(73) Assignees: Osaka University, Osaka (JP); Japan as Represented by Director General of National Institute of Health Sciences, Kanagawa (JP)

( * ) Notice: Subject to any disclaimer, the term of this patent is extended or adjusted under 35 U.S.C. 154(b) by 922 days.

(21) Appl. No.: 17/791,799

(22) PCT Filed: Feb. 18, 2021

(86) PCT No.: PCT/JP2021/006222
§ 371 (c)(1),
(2) Date: Jul. 8, 2022

(87) PCT Pub. No.: WO2021/167029
PCT Pub. Date: Aug. 26, 2021

(65) Prior Publication Data

US 2023/0340008 A1 Oct. 26, 2023

(30) Foreign Application Priority Data

Feb. 19, 2020 (JP) ................................ 2020-026646

(51) Int. Cl.
*C07H 21/02* (2006.01)

(52) U.S. Cl.
CPC .................................... *C07H 21/02* (2013.01)

(58) Field of Classification Search
None
See application file for complete search history.

(56) References Cited

U.S. PATENT DOCUMENTS 9,611,479 B2 * 4/2017 Obika .................... C07H 19/06
2011/0053881 A1 3/2011 Seth et al.
2017/0044528 A1 2/2017 Obika et al.
2019/0008886 A1 1/2019 Nakamori et al.
2020/0055890 A1 2/2020 Obika et al.

FOREIGN PATENT DOCUMENTS

WO 2019009298 A1 1/2019
WO 2020027227 A1 2/2020

OTHER PUBLICATIONS

S. Obika et al., Tetrahedron Letters, 1997, vol. 38, pp. 8735-8738.
S. Singh et al., Chem. Commun., 1998, pp. 455-456.
E. Swayze et al., Nucleic Acids Research., 2007, vol. 35, No. 2, pp. 687-700.
P.P. Seth et al., J. Org. Chem., 2010, 75, pp. 1569-1581.
T. Yamaguchi et al., Chem. Commun., 2015, 51, pp. 9737-9740.
M. Kuwahara et al., Nucleic Acids Research., 2008, vol. 36, No. 13, pp. 4257-4265.
Ludger et al., “Biosynthesis and Metabolism of Cyclopropane Rings in Natural Compounds”, Chem. Rev. 2003, 103, pp. 1625-1647.
Testa et al., “Organic Stereochemistry”, Hel. Chimica Acta, vol. 96, 2013.
PCT/JP2021/006222; PCT International Search Report of the International Searching Authority dated Apr. 5, 2021 and ts English translation.

* cited by examiner

*Primary Examiner* — Patrick T Lewis
(74) *Attorney, Agent, or Firm* — Renner, Otto, Boisselle & Sklar, LLP

(57) ABSTRACT

Disclosed are a bridged nucleoside and a nucleotide using the same. The nucleoside of the present invention is represented by the formula (I) below. The bridged nucleoside of the present invention is usable as a substitute for a phosphorothioate-modified nucleic acid, which has a risk of, for example, accumulation in a specific organ. The bridged nucleoside also has excellent industrial productivity.

[Chemical Formula 1]

(I)

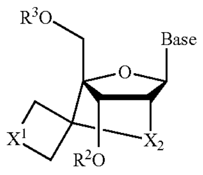

10 Claims, 3 Drawing Sheets

Specification includes a Sequence Listing.

[FIG.1]
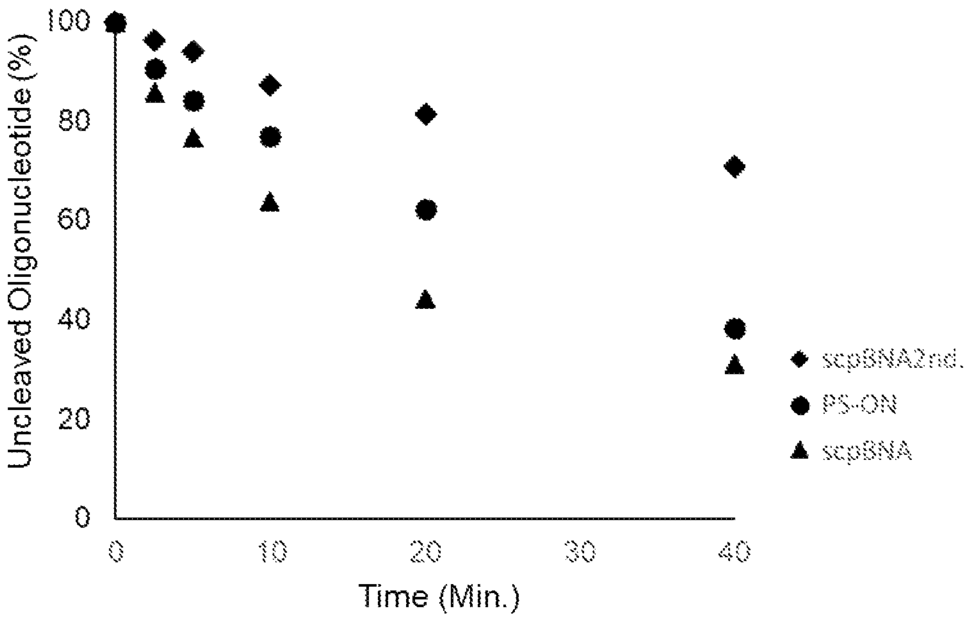

[Fig. 2]
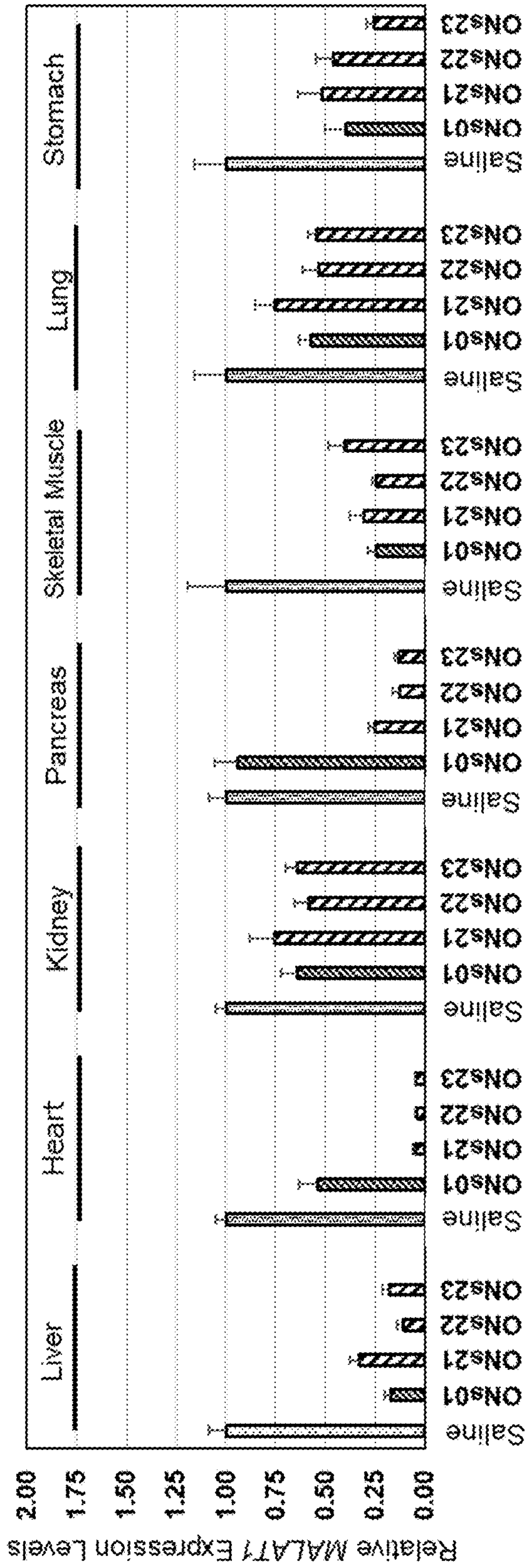

[Fig. 3]
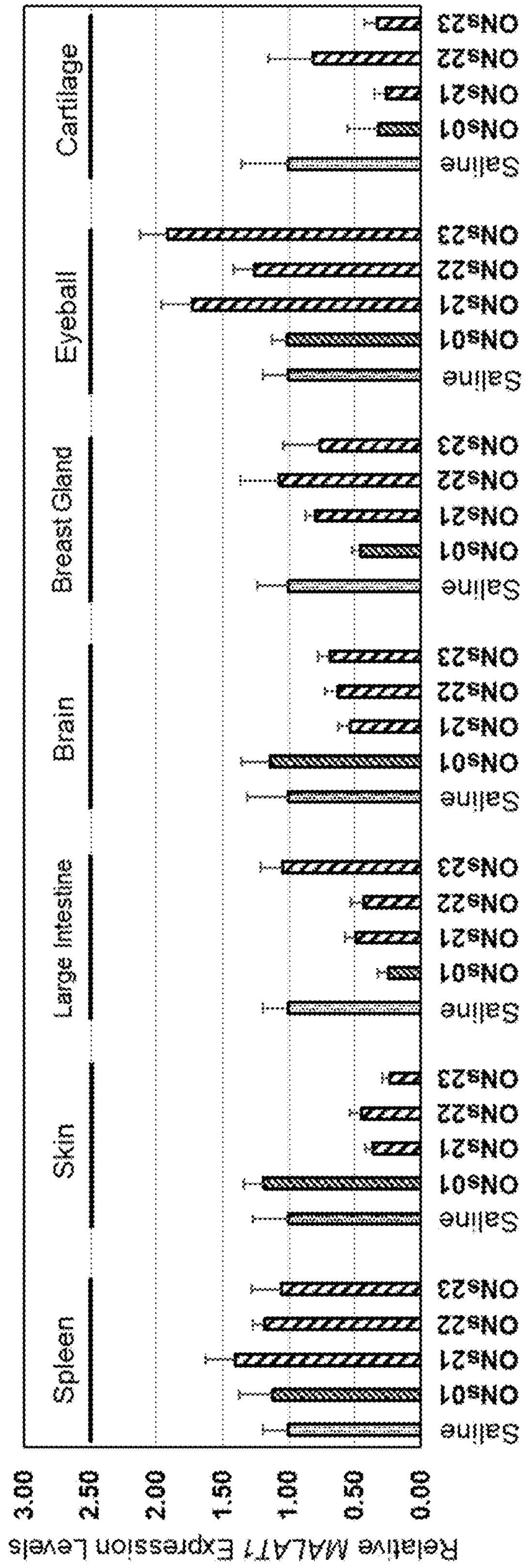

SEQUENCE LISTING

<160> NUMBER OF SEQ ID NOS: 17

<210> SEQ ID NO 1
<211> LENGTH: 12
<212> TYPE: DNA
<213> ORGANISM: Artificial Sequence
<220> FEATURE:
<223> OTHER INFORMATION: ON1
<220> FEATURE:
<221> NAME/KEY: modified_base
<222> LOCATION: (6)..(6)
<223> OTHER INFORMATION: t = scpBNA2nd-t

<400> SEQUENCE: 1
gcgttttttg ct 12

<210> SEQ ID NO 2
<211> LENGTH: 12
<212> TYPE: DNA
<213> ORGANISM: Artificial Sequence
<220> FEATURE:
<223> OTHER INFORMATION: ON2
<220> FEATURE:
<221> NAME/KEY: modified_base
<222> LOCATION: (4)..(4)
<223> OTHER INFORMATION: t = scpBNA2nd-t
<220> FEATURE:
<221> NAME/KEY: modified_base
<222> LOCATION: (6)..(6)
<223> OTHER INFORMATION: t = scpBNA2nd-t
<220> FEATURE:
<221> NAME/KEY: modified_base
<222> LOCATION: (8)..(8)
<223> OTHER INFORMATION: t = scpBNA2nd-t

<400> SEQUENCE: 2
gcgttttttg ct 12

<210> SEQ ID NO 3
<211> LENGTH: 12
<212> TYPE: DNA
<213> ORGANISM: Artificial Sequence
<220> FEATURE:
<223> OTHER INFORMATION: ON3
<220> FEATURE:
<221> NAME/KEY: modified_base
<222> LOCATION: (5)..(8)
<223> OTHER INFORMATION: t = scpBNA2nd-t

<400> SEQUENCE: 3
gcgttttttg ct 12

<210> SEQ ID NO 4
<211> LENGTH: 12
<212> TYPE: DNA
<213> ORGANISM: Artificial Sequence
<220> FEATURE:
<223> OTHER INFORMATION: ON4
<220> FEATURE:
<221> NAME/KEY: modified_base
<222> LOCATION: (4)..(9)
<223> OTHER INFORMATION: t = scpBNA2nd-t

<400> SEQUENCE: 4
gcgttttttg ct 12

<210> SEQ ID NO 5
<211> LENGTH: 12
<212> TYPE: DNA
<213> ORGANISM: Artificial Sequence

<220> FEATURE:
<223> OTHER INFORMATION: ON9

<400> SEQUENCE: 5 gcgtttttg ct 12

<210> SEQ ID NO 6
<211> LENGTH: 12
<212> TYPE: RNA
<213> ORGANISM: Artificial Sequence
<220> FEATURE:
<223> OTHER INFORMATION: ss oligoRNA

<400> SEQUENCE: 6
agcaaaaaac gc 12

<210> SEQ ID NO 7
<211> LENGTH: 12
<212> TYPE: DNA
<213> ORGANISM: Artificial Sequence
<220> FEATURE:
<223> OTHER INFORMATION: ss oligoDNA

<400> SEQUENCE: 7
agcaaaaaac gc 12

<210> SEQ ID NO 8
<211> LENGTH: 16
<212> TYPE: DNA
<213> ORGANISM: Artificial Sequence
<220> FEATURE:
<223> OTHER INFORMATION: ONs21
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: c or t = scpBNA2nd
<220> FEATURE:
<221> NAME/KEY: modified_base
<222> LOCATION: (1)..(16)
<223> OTHER INFORMATION: phosphorothioated
<220> FEATURE:
<221> NAME/KEY: modified_base
<222> LOCATION: (3)..(3)
<223> OTHER INFORMATION: a = 2',4'-BNA/LNA
<220> FEATURE:
<221> NAME/KEY: modified_base
<222> LOCATION: (14)..(14)
<223> OTHER INFORMATION: t = scpBNA2nd
<220> FEATURE:
<221> NAME/KEY: modified_base
<222> LOCATION: (15)..(15)
<223> OTHER INFORMATION: g = 2',4'-BNA/LNA
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (16)..(16)
<223> OTHER INFORMATION: c = scpBNA2nd

<400> SEQUENCE: 8
ctagttcact gaatgc 16

<210> SEQ ID NO 9
<211> LENGTH: 16
<212> TYPE: DNA

<213> ORGANISM: Artificial Sequence
<220> FEATURE:
<223> OTHER INFORMATION: ONs22
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: c or t = scpBNA2nd
<220> FEATURE:
<221> NAME/KEY: modified_base
<222> LOCATION: (3)..(3)
<223> OTHER INFORMATION: a = 2',4'-BNA/LNA
<220> FEATURE:
<221> NAME/KEY: modified_base
<222> LOCATION: (4)..(13)
<223> OTHER INFORMATION: phosphorothioated
<220> FEATURE:
<221> NAME/KEY: modified_base
<222> LOCATION: (14)..(14)
<223> OTHER INFORMATION: t = scpBNA2nd
<220> FEATURE:
<221> NAME/KEY: modified_base
<222> LOCATION: (15)..(15)
<223> OTHER INFORMATION: g = 2',4'-BNA/LNA
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (16)..(16)
<223> OTHER INFORMATION: c = scpBNA2nd

<400> SEQUENCE: 9
ctagttcact gaatgc 16

<210> SEQ ID NO 10
<211> LENGTH: 16
<212> TYPE: DNA
<213> ORGANISM: Artificial Sequence
<220> FEATURE:
<223> OTHER INFORMATION: ONs23
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: c or t = scpBNA2nd
<220> FEATURE:
<221> NAME/KEY: modified_base
<222> LOCATION: (3)..(3)
<223> OTHER INFORMATION: a = 2',4'-BNA/LNA
<220> FEATURE:
<221> NAME/KEY: modified_base
<222> LOCATION: (4)..(14)
<223> OTHER INFORMATION: phosphorothioated
<220> FEATURE:
<221> NAME/KEY: modified_base
<222> LOCATION: (14)..(14)
<223> OTHER INFORMATION: t = scpBNA2nd
<220> FEATURE:
<221> NAME/KEY: modified_base
<222> LOCATION: (15)..(15)
<223> OTHER INFORMATION: g = 2',4'-BNA/LNA
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (16)..(16)
<223> OTHER INFORMATION: c = scpBNA2nd
<220> FEATURE:
<221> NAME/KEY: modified_base
<222> LOCATION: (16)..(16)
<223> OTHER INFORMATION: phosphorothioated

<400> SEQUENCE: 10
ctagttcact gaatgc 16

<210> SEQ ID NO 11
<211> LENGTH: 14
<212> TYPE: DNA
<213> ORGANISM: Artificial Sequence
<220> FEATURE:
<223> OTHER INFORMATION: ONd1
<220> FEATURE:
<221> NAME/KEY: modified_base
<222> LOCATION: (1)..(1)
<223> OTHER INFORMATION: g = 2', 4'-BNA/LNA
<220> FEATURE:
<221> NAME/KEY: modified_base
<222> LOCATION: (2)..(14)
<223> OTHER INFORMATION: phosphorothioated
<220> FEATURE:
<221> NAME/KEY: modified_base
<222> LOCATION: (2)..(3)
<223> OTHER INFORMATION: t = scpBNA2nd
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (12)..(12)
<223> OTHER INFORMATION: c = 2', 4'-BNA/LNA
<220> FEATURE:
<221> NAME/KEY: modified_base
<222> LOCATION: (13)..(13)
<223> OTHER INFORMATION: t = scpBNA2nd
<220> FEATURE:
<221> NAME/KEY: modified_base
<222> LOCATION: (14)..(14)
<223> OTHER INFORMATION: a = 2', 4'-BNA/LNA

<400> SEQUENCE: 11
gttatgccac ccta 14

<210> SEQ ID NO 12
<211> LENGTH: 14
<212> TYPE: DNA
<213> ORGANISM: Artificial Sequence
<220> FEATURE:
<223> OTHER INFORMATION: ONd0
<220> FEATURE:
<221> NAME/KEY: modified_base
<222> LOCATION: (1)..(3)
<223> OTHER INFORMATION: g or t = 2', 4'-BNA/LNA
<220> FEATURE:
<221> NAME/KEY: modified_base
<222> LOCATION: (12)..(14)
<223> OTHER INFORMATION: c, t or a = 2', 4'-BNA/LNA
<220> FEATURE:
<221> NAME/KEY: modified_base
<222> LOCATION: (12)..(12)
<223> OTHER INFORMATION: m5c

<400> SEQUENCE: 12
gttatgccac ccta 14

<210> SEQ ID NO 13
<211> LENGTH: 16
<212> TYPE: DNA
<213> ORGANISM: Artificial Sequence
<220> FEATURE:

```
<223> OTHER INFORMATION: ONs01
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(3)
<223> OTHER INFORMATION: c, t or a = 2',4'-BNA/LNA
<220> FEATURE:
<221> NAME/KEY: modified_base
<222> LOCATION: (14)..(16)
<223> OTHER INFORMATION: t, g or c = 2',4'-BNA/LNA
<220> FEATURE:
<221> NAME/KEY: modified_base
<222> LOCATION: (16)..(16)
<223> OTHER INFORMATION: m5c

<400> SEQUENCE: 13

ctagttcact gaatgc                                                16


<210> SEQ ID NO 14
<211> LENGTH: 20
<212> TYPE: DNA
<213> ORGANISM: Artificial Sequence
<220> FEATURE:
<223> OTHER INFORMATION: MALAT1 forward

<400> SEQUENCE: 14

acattccttg aggtcggcaa                                            20


<210> SEQ ID NO 15
<211> LENGTH: 20
<212> TYPE: DNA
<213> ORGANISM: Artificial Sequence
<220> FEATURE:
<223> OTHER INFORMATION: MALAT1 reverse

<400> SEQUENCE: 15

cacccgcaaa ggcctacata                                            20


<210> SEQ ID NO 16
<211> LENGTH: 19
<212> TYPE: DNA
<213> ORGANISM: Artificial Sequence
<220> FEATURE:
<223> OTHER INFORMATION: GAPDH forward

<400> SEQUENCE: 16

tcaccaccat ggagaaggc                                             19


<210> SEQ ID NO 17
<211> LENGTH: 20
<212> TYPE: DNA
<213> ORGANISM: Artificial Sequence
<220> FEATURE:
<223> OTHER INFORMATION: GAPDH reverse

<400> SEQUENCE: 17

gctaagcagt tggtggtgca                                            20
```

BRIDGED NUCLEOSIDE AND NUCLEOTIDE USING SAME

This application is a national phase of International Application No. PCT/JP2021/006222 filed 18 Feb. 2021, which claims priority to Japan Application No. 2020-026646 filed 19 Feb. 2020, each of which is hereby incorporated herein by reference in its entirety.

TECHNICAL FIELD

The present invention relates to a bridged nucleoside and a nucleotide using the same. More specifically, the invention relates to a bridged nucleoside that has good nuclease-resistant ability and can be produced with high efficiency, and a nucleotide using the same.

BACKGROUND ART

Various artificial nucleic acids having high binding affinity for DNA or RNA are applicable to gene diagnosis and oligonucleotide therapeutics, and various types of artificial nucleic acids have been developed. In particular, 2',4'-BNA (2',4'-bridged nucleic acid, also known as LNA) in which the conformation of the sugar moiety in the nucleic acid is immobilized on the N-conformation through cross-linking has high binding affinity for a single-stranded RNA (ssRNA) and is expected as oligonucleotide therapeutics that can be used in various applications such as the antisense therapies (Non-Patent Documents 1 and 2). However, 2',4'-BNA has the problems of having low enzyme resistance and being likely to induce hepatotoxicity (Non-Patent Document 3).

In contrast, it has been reported that an artificial nucleic acid obtained by introducing a substituent such as a methyl group or a methoxy methyl group at the 6' position of 2',4'-BNA has improved binding affinity for ssRNA and great enzyme-resistant ability (Non-Patent Document 4). However, introduction of such a substituent at the 6' position may result in the production of isomers, and complicated separation operations will be required.

Meanwhile, it has been reported that an artificial nucleic acid (scpBNA) obtained by introducing a cyclopropyl group at the 6' position can be synthesized through a synthetic pathway in which isomer separation is not required, and has high binding affinity for ssRNA and good enzyme-resistant ability (Patent Document 1 and Non-Patent Document 5). However, it is hard to say that the yields of various products obtained in the synthetic pathway of scpBNA are sufficiently satisfactory. Development of artificial nucleic acids that are applicable to industrial applications and can be synthesized in higher yields has been desired.

RELATED ART DOCUMENTS

Patent Documents

Patent Document 1: WO2015/125783

Non-Patent Document

Non-Patent Document 1: S. Obika et al., Tetrahedron Lett., 1997, 38, 8735-8738

Non-Patent Document 2: S. Singh et al., Chem. Comm., 1998, 455-456

Non-Patent Document 3: E. Swayze et al., Nucleic Acids Res., 2007, 35, 687-700

Non-Patent Document 4: P. P. Seth et al., J. Org. Chem., 2010, 75, 1569-1581

Non-Patent Document 5: T. Yamaguchi et al., Chem. Comm., 2015, 51, 9737-9740

SUMMARY OF INVENTION

Problem to be Solved by the Invention

The present invention was made to address the above problems and it is an object thereof to provide a bridged nucleoside in which a substituent is introduced at the 6' position and that can be produced in a higher yield without involving complicated operations such as isomer separation, and a nucleotide using the same.

Means for Solving the Problem

The present invention provides a compound represented by a formula (I) below or a salt thereof.

[Chemical Formula 1]

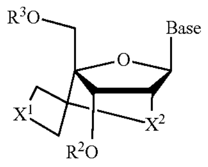

(I)

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms;

$R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms;

$X^1$ is an alkylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms, or an alkenylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms; and $X^2$ is an oxygen atom, a sulfur atom, —NH—, —$N(CH_3)$—, or a methylene group.

In one embodiment, the above formula (I) is represented by a formula below:

[Chemical Formula 2]

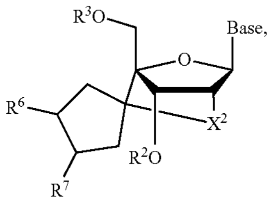

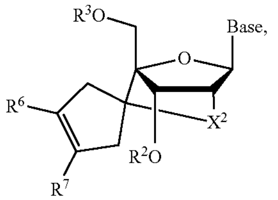

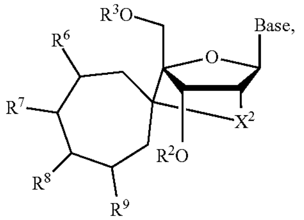

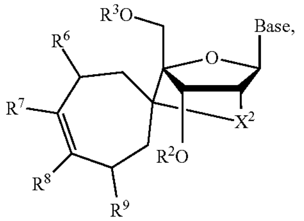

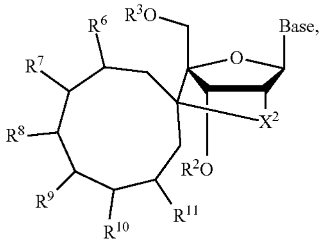

or

-continued

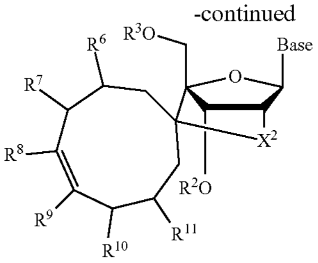

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, $R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms, $X^2$is an oxygen atom, a sulfur atom, —NH—, —$N(CH_3)$—, or a methylene group, and $R^6$, $R^7$, $R^8$, $R^9$, $R^{10}$, and $R^{11}$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms.

In one embodiment, the above formula (I) is represented by a formula below:

[Chemical Formula 3]

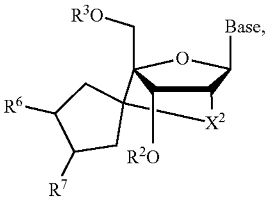

or

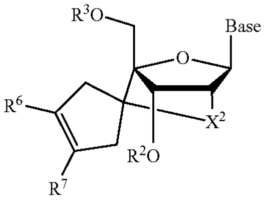

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, $R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms, $X^2$ is an oxygen atom, a sulfur atom, —NH—, —$N(CH_3)$—, or a methylene group, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms.

In one embodiment, the Base in the formula (I) is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

In one embodiment, the Base in the formula (I) is a group represented by a formula below:

[Chemical Formula 4]

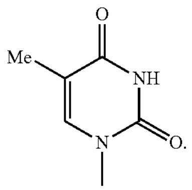

The present invention also provides an oligonucleotide containing at least one nucleoside structure represented by a formula (II) below or a pharmacologically acceptable salt thereof:

[Chemical Formula 5]

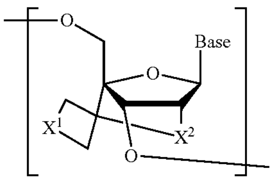

(II)

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms;

$X^1$ is an alkylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or $—OR^{5b}$, where $R^{5b}$ is a hydrogen atom or a linear alkyl group having 1 to 3 carbon atoms, or an alkenylene group having 2 to 8 carbon atoms that may have undergone substitution by a linear alkyl group having 1 to 3 carbon atoms, $—NHR^{4b}$, where $R^{4b}$ is a hydrogen atom or a linear alkyl group having 1 to 3 carbon atoms, or $—OR^{5b}$, where $R^{5b}$ is a hydrogen atom or a linear alkyl group having 1 to 3 carbon atoms; and $X^2$ is an oxygen atom, a sulfur atom, —NH—, $—N(CH_3)—$, or a methylene group.

In one embodiment, the above formula (II) is represented by a formula below:

[Chemical Formula 6]

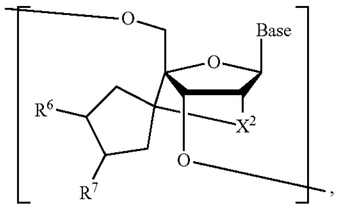

,

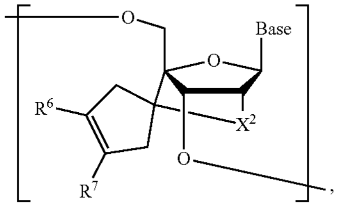

,

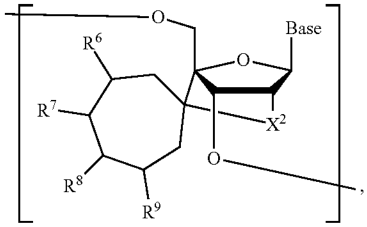

,

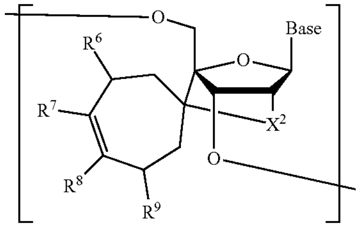

,

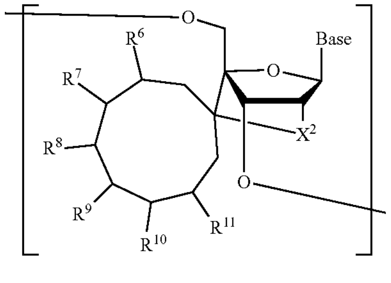

, or

-continued

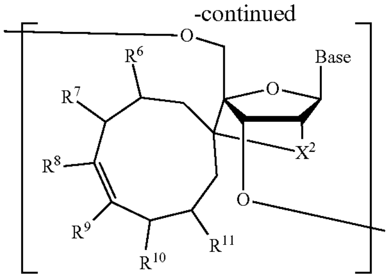

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms;

$X^2$ is an oxygen atom, a sulfur atom, —NH—, $—N(CH_3)—$, or a methylene group, and $R^6$, $R^7$, $R^8$, $R^9$, $R^{10}$, and $R^{11}$ are each independently a hydrogen atom, a linear alkyl group having 1 to 3 carbon atoms, $—NHR^{4b}$, where $R^{4b}$ is a hydrogen atom or a linear alkyl group having 1 to 3 carbon atoms, or $—OR^5$, where $R^5$ is a hydrogen atom or a linear alkyl group having 1 to 3 carbon atoms.

In one embodiment, the above formula (II) is represented by a formula below:

[Chemical Formula 7]

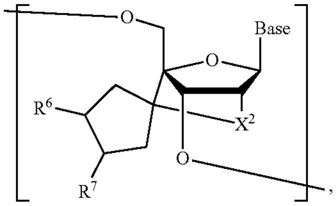

, or

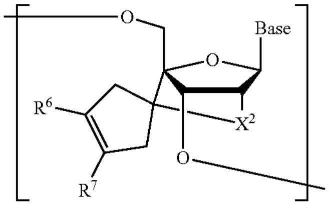

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms;

$X^2$ is an oxygen atom, a sulfur atom, —NH—, —N($CH_3$)—, or a methylene group, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms.

The present invention also provides a method for producing the above oligonucleotide or pharmacologically acceptable salt thereof, comprising:

synthesizing an oligonucleotide using a compound represented by a formula (I) below or a pharmacologically acceptable salt thereof:

[Chemical Formula 8]

(I)

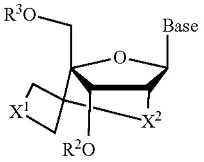

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms;

$R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms;

$X^1$ is an alkylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms, or an alkenylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms; and $X^2$ is an oxygen atom, a sulfur atom, —NH—, —N($CH_3$)—, or a methylene group.

Effects of the Invention

According to the present invention, provided are a novel bridged nucleoside modified at the 6'-position that has high binding affinity for ssRNA and good enzyme-resistant ability, and a nucleotide using the same. A bridged nucleoside according to the present invention also has high industrial productivity because isomer separation is not involved in the production thereof.

BRIEF DESCRIPTION OF DRAWINGS

FIG. 1 is a graph showing changes in the percentage of uncleaved oligonucleotides over time when different types of oligonucleotides having the sequence of 5'-TTTTTTTTTX-3' were treated with 3'-exonuclease.

FIG. 2 is a graph showing relative MALAT1 expression levels in various tissues of mice in administration of various oligonucleotides.

FIG. 3 is a graph showing relative MALAT1 expression levels in various tissues of mice in administration of various oligonucleotides.

DESCRIPTION OF EMBODIMENTS

The following definitions shall apply throughout the specification.

The term "linear alkyl group having 1 to 6 carbon atoms" as used herein refers to any linear alkyl group having 1 to 6 carbon atoms, and specifically to a methyl group, an ethyl group, an n-propyl group, an n-butyl group, an n-pentyl group, or an n-hexyl group. Also, the term "linear alkyl group having 1 to 3 carbon atoms" refers to any linear alkyl group having 1 to 3 carbon atoms, and specifically to a methyl group, an ethyl group, or an n-propyl group. On the other hand, the term "alkyl group having 1 to 6 carbon atoms" refers to any linear, branched, or cyclic alkyl group having 1 to 6 carbon atoms.

The term "linear alkoxy group having 1 to 6 carbon atoms" as used herein encompasses alkoxy groups including any linear alkyl groups having 1 to 6 carbon atoms. Examples thereof include a methoxy group, an ethoxy group, and an n-propoxy group. On the other hand, the term "alkoxy group having 1 to 6 carbon atoms" refers to any linear, branched, or cyclic alkoxy group having 1 to 6 carbon atoms. The term "linear alkoxy group having 1 to 6 carbon atoms that may have undergone substitution by a linear alkoxy group having 1 to 6 carbon atoms" refers to the "linear alkoxy group having 1 to 6 carbon atoms" as well as an alkoxy group obtained by substituting one or more hydrogen atoms included in the "linear alkoxy group having 1 to 6 carbon atoms" with another or other "linear alkoxy groups having 1 to 6 carbon atoms" that may be the same or different. Examples of such "linear alkoxy group having 1 to 6 carbon atoms that may have undergone substitution by a linear alkoxy group having 1 to 6 carbon atoms" include a methoxy group, an ethoxy group, an n-propoxy group, a methoxymethoxy group, an ethoxymethoxy group, an n-propoxymethoxy group, a methoxyethoxy group (e.g., a 2-methoxyethoxy group), an ethoxyethoxy group (e.g., a 2-ethoxyethoxy group), and an n-propoxyethoxy group.

The term "cyanoalkoxy group having 1 to 6 carbon atoms" as used herein refers to a group obtained by substituting at least one hydrogen atom included in any linear, branched, or cyclic alkoxy group having 1 to 6 carbon atoms with a cyano group.

The term "linear alkylthio group having 1 to 6 carbon atoms" as used herein encompasses alkylthio groups including any linear alkyl groups having 1 to 6 carbon atoms. Examples thereof include a methylthio group, an ethylthio group, and an n-propylthio group. On the other hand, the term "alkylthio group having 1 to 6 carbon atoms" refers to any linear, branched, or cyclic alkylthio group having 1 to 6 carbon atoms.

The term "linear alkylamino group having 1 to 6 carbon atoms" as used herein encompasses alkylamino groups including one or two alkylamino groups with any linear alkyl group having 1 to 6 carbon atoms. Examples thereof include a methylamino group, a dimethylamino group, an ethylamino group, a methylethylamino group, and a diethylamino group.

The term "alkyl group having 1 to 7 carbon atoms that may form a branch or a ring" as used herein encompasses any linear alkyl groups having 1 to 7 carbon atoms, any branched alkyl groups having 3 to 7 carbon atoms, and any cyclic alkyl groups having 3 to 7 carbon atoms. Such groups may also be referred to merely as "lower alkyl groups". Examples of any linear alkyl groups having 1 to 7 carbon atoms include a methyl group, an ethyl group, an n-propyl group, an n-butyl group, an n-pentyl group, an n-hexyl group, and an n-heptyl group; examples of any branched alkyl groups having 3 to 7 carbon atoms include an isopropyl group, an isobutyl group, a tert-butyl group, and an isopentyl group; and examples of any cyclic alkyl groups having 3 to 7 carbon atoms include a cyclobutyl group, a cyclopentyl group, and a cyclohexyl group.

The term "alkenyl group having 2 to 7 carbon atoms that may form a branch or a ring" as used herein encompasses any linear alkenyl groups having 2 to 7 carbon atoms, any branched alkenyl groups having 3 to 7 carbon atoms, and any cyclic alkenyl groups having 3 to 7 carbon atoms. Such groups may also be referred to merely as "lower alkenyl groups". Examples of any linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, and a 1-hexenyl group; examples of any branched alkenyl groups having 3 to 7 carbon atoms include an isopropenyl group, a 1-methyl-1-propenyl group, a 1-methyl-2-propenyl group, a 2-methyl-1-propenyl group, a 2-methyl-2-propenyl group, and a 1-methyl-2-butenyl group; and examples of any cyclic alkenyl groups having 3 to 7 carbon atoms include a cyclobutenyl group, a cyclopentenyl group, and a cyclohexenyl group.

The term "aryl group having 3 to 10 carbon atoms that may have a heteroatom" as used herein encompasses any aryl groups having 6 to 10 carbon atoms that are constituted by only a hydrocarbon, and any heteroaryl groups having 3 to 12 carbon atoms obtained by substituting at least one carbon atom included in the ring structure of the above-mentioned aryl groups with a heteroatom (e.g., a nitrogen atom, an oxygen atom, or a sulfur atom, or a combination thereof). Examples of the aryl groups having 6 to 10 carbon atoms include a phenyl group, a naphthyl group, an indenyl group, and an azulenyl group; and examples of any heteroaryl groups having 3 to 12 carbon atoms include a pyridyl group, a pyrrolyl group, a quinolyl group, an indolyl group, an imidazolyl group, a furyl group, and a thienyl group.

Examples of the term "aralkyl group with an aryl moiety having 3 to 12 carbon atoms that may have a heteroatom" as used herein include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, and a 3-thienylpropyl group.

Examples of the term "acyl group" as used herein include aliphatic acyl groups and aromatic acyl groups. Specifically, examples of the aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group, and a heneicosanoyl group; carboxylated alkylcarbonyl groups such as a succinoyl group, a glutaroyl group, and an adipoyl group; halogeno lower-alkyl-carbonyl groups such as a chloroacetyl group, a dichloroacetyl group, a trichloroacetyl group, and a trifluoroacetyl group; lower-alkoxy-lower-alkyl-carbonyl groups such as a methoxyacetyl group; and unsaturated alkylcarbonyl groups such as an (E)-2-methyl-2-butenoyl group. Examples of the aromatic acyl groups include arylcarbonyl groups such as a benzoyl group, an α-naphthoyl group, and a β-naphthoyl group; halogeno arylcarbonyl groups such as a 2-bromobenzoyl group and a 4-chlorobenzoyl group; low-alkylated arylcarbonyl groups such as a 2,4,6-trimethylbenzoyl group and a 4-toluoyl group; low-alkoxylated arylcarbonyl groups such as a 4-anisoyl group: carboxylated arylcarbonyl groups such as a 2-carboxybenzoyl group, a 3-carboxybenzoyl group, and a 4-carboxybenzoyl group; nitrated arylcarbonyl groups such as a 4-nitrobenzoyl group and a 2-nitrobenzoyl group; low-alkoxycarbonylated arylcarbonyl groups such as a 2-(methoxycarbonyl)benzoyl group; and arylated arylcarbonyl groups such as a 4-phenylbenzoyl group. A formyl group, an acetyl group, a propionyl group, a butyryl group, an isobutyryl group, a pentanoyl group, a pivaloyl group, and a benzoyl group are favorable.

The term "alkylene group having 2 to 8 carbon atoms" as used herein refers to a divalent group having 2 to 8 carbon atoms constituted by repeating methylene groups ($—CH_2—$). Specific examples thereof include $—CH_2CH_2—$, $—CH_2CH_2CH_2CH_2—$, and $—CH_2CH_2CH_2CH_2CH_2CH_2—$. Furthermore, the term “alkylene group having 2 to 8 carbon atoms that may have undergone substitution by a linear alkyl group having 1 to 3 carbon atoms, $—NHR^{4b}$, where $R^{4b}$ is a hydrogen atom or a linear alkyl group having 1 to 3 carbon atoms, or $—OR^{5b}$, where $R^{5b}$ is a hydrogen atom or a linear alkyl group having 1 to 3 carbon atoms” refers to a group obtained by substituting at least one hydrogen atom included in the alkylene group having 2 to 8 carbon atoms that is unsubstituted, that is, a divalent group having 2 to 8 carbon atoms that is constituted only by repeating methylene groups, by a linear alkyl group having 1 to 3 carbon atoms, $—NHR^{4b}$, or $—OR^{5b}$.

The term “alkenylene group having 2 to 8 carbon atoms” as used herein encompasses —CH═CH— and a divalent group having 2 to 8 carbon atoms constituted by a combination of at least one methylene group and one carbon-carbon double bond (—CH═CH—). Specific examples thereof include —CH═CH—, $—CH_2CH═CHCH_2—$, and $—CH_2CH_2CH═CHCH_2CH_2—$. Furthermore, the term “alkenylene group having 2 to 8 carbon atoms that may have undergone substitution by a linear alkyl group having 1 to 3 carbon atoms, $—NHR^{4b}$, where $R^{4b}$ is a hydrogen atom or a linear alkyl group having 1 to 3 carbon atoms, or $—OR^{5b}$, where $R^{5b}$ is a hydrogen atom or a linear alkyl group having 1 to 3 carbon atoms” refers to a group obtained by substituting at least one hydrogen atom included in the alkenylene group having 2 to 8 carbon atoms that is unsubstituted, by a linear alkyl group having 1 to 3 carbon atoms, $—NHR^{4b}$, or $—OR^{5b}$.

Examples of the term “silyl group” as used herein include tri-lower-alkyl-silyl groups such as a trimethylsilyl group, a triethylsilyl group, an isopropyldimethylsilyl group, a t-butyldimethylsilyl group, a methyldiisopropylsilyl group, a methyldi-t-butylsilyl group, and a triisopropylsilyl group; and tri-lower-alkyl-silyl groups that have undergone substitution by one or two aryl groups, such as a diphenylmethylsilyl group, a butyldiphenylbutylsilyl group, a diphenylisopropylsilyl group, and a phenyldiisopropylsilyl group. A trimethylsilyl group, a triethylsilyl group, a triisopropylsilyl group, a t-butyldimethylsilyl group, and a t-butyldiphenylsilyl group are favorable, and a trimethylsilyl group is more favorable.

Examples of the term “halogen atom” as used herein include a fluorine atom, a chlorine atom, a bromine atom, and an iodine atom. A fluorine atom or a chlorine atom is favorable.

“Protecting groups” in the terms “amino group protecting group for nucleic acid synthesis”, “hydroxy group protecting group for nucleic acid synthesis”, “hydroxy group protected by a protecting group for nucleic acid synthesis”, “phosphate group protected by a protecting group for nucleic acid synthesis”, and “mercapto group protected by a protecting group for nucleic acid synthesis” as used herein are not particularly limited as long as they can stably protect an amino group, a hydroxy group, a phosphate group, or a mercapto group during nucleic acid synthesis. Specifically, the protecting groups are stable under an acidic or neutral condition and can be cleaved using chemical techniques such as hydrogenolysis, hydrolysis, electrolysis, and photolysis. Examples of such protecting groups include lower alkyl groups, lower alkenyl groups, acyl groups, tetrahydropyranyl or tetrahydrothiopyranyl groups, tetrahydrofuranyl or tetrahydrothiofuranyl groups, silyl groups, lower-alkoxy-methyl groups, low-alkoxylated lower-alkoxy-methyl groups, halogeno lower-alkoxy-methyl groups, low-alkoxylated ethyl groups, halogenated ethyl groups, methyl groups that have undergone substitution by 1 to 3 aryl groups, “methyl groups that have undergone substitution by 1 to 3 aryl groups in which an aryl ring has undergone substitution by a lower alkyl group, lower alkoxy group, halogen atom, or cyano group”, lower-alkoxy-carbonyl groups, “aryl groups that have undergone substitution by a halogen atom, lower alkoxy group, or nitro group”, “lower-alkoxy-carbonyl groups that have undergone substitution by a halogen atom or tri-lower-alkyl-silyl group”, alkenyloxycarbonyl groups, and “aralkyloxycarbonyl groups in which an aryl ring may have undergone substitution by a lower alkoxy group or nitro group”.

More specific examples of the tetrahydropyranyl or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, and a 4-methoxytetrahydrothiopyran-4-yl group. Examples of the tetrahydrofuranyl or tetrahydrothiofuranyl groups include a tetrahydrofuran-2-yl group and a tetrahydrothiofuran-2-yl group. Examples of the lower-alkoxy-methyl groups include a methoxymethyl group, a 1,1-dimethyl-1-methoxymethyl group, an ethoxymethyl group, a propoxymethyl group, an isopropoxymethyl group, a butoxymethyl group, and a t-butoxymethyl group. An example of the low-alkoxylated lower-alkoxy-methyl groups is a 2-methoxyethoxymethyl group. Examples of the halogeno lower-alkoxy-methyl groups include a 2,2,2-trichloroethoxymethyl group and a bis(2-chloroethoxy)methyl group. Examples of the low-alkoxylated ethyl groups include a 1-ethoxyethyl group and a 1-(isopropoxy)ethyl group. An example of the halogenated ethyl groups is a 2,2,2-trichloroethyl group. Examples of the methyl groups that have undergone substitution by 1 to 3 aryl groups include a benzyl group, an α-naphthylmethyl group, a β-naphthylmethyl group, a diphenylmethyl group, a triphenylmethyl group, an α-naphthyldiphenylmethyl group, and a 9-anthrylmethyl group. Examples of the “methyl groups that have undergone substitution by 1 to 3 aryl groups in which an aryl ring has undergone substitution by a lower alkyl group, lower alkoxy group, halogen atom, or cyano group” include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, and a 4-cyanobenzyl group. Examples of the lower-alkoxy-carbonyl groups include a methoxycarbonyl group, an ethoxycarbonyl group, a t-butoxycarbonyl group, and an isobutoxycarbonyl group. Examples of the “aryl groups that have undergone substitution by a halogen atom, lower alkoxy group, or nitro group” include a 4-chlorophenyl group, a 2-fluorophenyl group, a 4-methoxyphenyl group, a 4-nitrophenyl group, and a 2,4-dinitrophenyl group. Examples of the “lower-alkoxy-carbonyl groups that have undergone substitution by a halogen atom or tri-lower-alkyl-silyl group” include a 2,2,2-trichloroethoxycarbonyl group and 2-trimethylsilylethoxycarbonyl group. Examples of the alkenyloxycarbonyl groups include a vinyloxycarbonyl group and an aryloxycarbonyl group. Examples of the “aralkyloxycarbonyl groups in which an aryl ring may have undergone substitution by a lower alkoxy group or nitro group” include a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group.

In one embodiment, examples of the "hydroxy group protecting group for nucleic acid synthesis" include aliphatic acyl groups, aromatic acyl groups, methyl groups that have undergone substitution by 1 to 3 aryl groups, "methyl groups that have undergone substitution by 1 to 3 aryl groups in which an aryl ring has undergone substitution by a lower alkyl, lower alkoxy, halogen, or cyano group", and silyl groups. Alternatively, in one embodiment, examples of the "hydroxy group protecting group for nucleic acid synthesis" include an acetyl group, a benzoyl group, a benzyl group, a p-methoxybenzoyl group, a dimethoxytrityl group, a monomethoxytrityl group, a tert-butyldiphenylsilyl group, a tert-butyldimethylsilyl (TBDMS) group, a [(triisopropylsilyl)oxy]methyl (TOM) group, a [(2-nitrobenzyl)oxy]methyl (NBOM) group, a bis(acetoxyethoxy)methyl ether (ACE) group, a tetrahydro-4-methoxy-2H-pyran-2-yl (Mthp) group, a 1-(2-cyanoethoxy)ethyl (CEE) group, a 2-cyanoethoxymethyl (CEM) group, a tert-butyldithiomethyl (DTM) group, a 2-(4-tolylsulfonyl)ethoxymethyl (TEM) group, and a 4-(N-dichloroacetyl-N-methylamino)benzyloxymethyl (4-MABOM) group.

In one embodiment, examples of the protecting group used for the "hydroxy group protected by a protecting group for nucleic acid synthesis" include aliphatic acyl groups, aromatic acyl groups, "methyl groups that have undergone substitution by 1 to 3 aryl groups", "aryl groups that have undergone substitution by a halogen atom, lower alkoxy group, or nitro group", lower alkyl groups, and lower alkenyl groups. Alternatively, in one embodiment, examples of the protecting group used for the "hydroxy group protected by a protecting group for nucleic acid synthesis" include a benzoyl group, a benzyl group, a 2-chlorophenyl group, a 4-chlorophenyl group, and a 2-propenyl group.

In one embodiment, examples of the "amino group protecting group for nucleic acid synthesis" include acyl groups, and a benzoyl group is favorable.

In one embodiment, examples of the "protecting group" used for the "phosphate group protected by a protecting group for nucleic acid synthesis" include lower alkyl groups, lower alkyl groups that have undergone substitution by a cyano group, aralkyl groups, "aralkyl groups in which an aryl ring has undergone substitution by a nitro group or halogen atom", and "aryl groups that have undergone substitution by a lower alkyl group, halogen atom, or nitro group". Alternatively, in one embodiment, examples of the "protecting group" used for the "phosphate group protected by a protecting group for nucleic acid synthesis" include a 2-cyanoethyl group, a 2,2,2-trichloroethyl group, a benzyl group, a 2-chlorophenyl group, and a 4-chlorophenyl group.

In one embodiment, examples of the "protecting group" used for the "mercapto group protected by a protecting group for nucleic acid synthesis" include aliphatic acyl groups and aromatic acyl groups, and a benzoyl group is favorable.

In this specification, among groups represented by $—P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms, a group in which $R^{4a}$ is $OR^{4c}$ and $R^{5a}$ is $NR^{5c}$ is referred to as a "phosphoramidite group", where an example of $R^{4c}$ is a cyanoalkoxy group having 1 to 6 carbon atoms, and an example of $R^{5c}$ is an alkyl group having 1 to 6 carbon atoms. Favorable examples of the phosphoramidite group include a group represented by a formula $—P(OC_2H_4CN)(N(iPr)_2)$ and a group represented by a formula $—P(OCH_3)(N(iPr)_2)$. In these formulae, iPr represents an isopropyl group.

The terms "nucleoside" and "nucleoside analogue" as used herein refer to non-natural nucleosides of "nucleosides" in which a purine base or a pyrimidine base binds to sugar, as well as those in which a heteroaromatic ring or an aromatic hydrocarbon ring other than purine and pyrimidine that can serve as a substitute for a purine or pyrimidine base binds to sugar.

The terms "artificial oligonucleotide" and "oligonucleotide analogue" as used herein refer to non-natural derivatives of "oligonucleotides" in which, for example, two to fifty of the same or different "nucleosides" or "nucleoside analogues" are bound via phosphodiester bonds. Favorable examples of such analogues include sugar derivatives with sugar moieties modified; thioated derivatives with phosphate diester moieties thioated; esters with terminal phosphate moieties esterified; and amides in which amino groups on purine bases are amidated.

The term "salt thereof" as used herein refers to a salt of a compound represented by the formula (I) or (II) of the present invention. Examples of such salt include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkanesulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

The term "pharmacologically acceptable salt thereof" as used herein refers to a salt of an oligonucleotide analogue containing at least one nucleoside structure represented by the formula (II) of the present invention. Examples of such salts include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkane-sulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

Hereinafter, the present invention will be described in detail.

Bridged Nucleoside

A bridged nucleoside according to the present invention is represented by a formula (I) below:

[Chemical Formula 9]

(I)

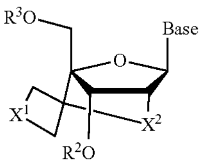

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, $R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms, $X^1$ is an alkylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms, or an alkenylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms, and $X^2$ is an oxygen atom, a sulfur atom, —NH—, —$N(CH_3)$—, or a methylene group.

In the formula (I) above, "Base" is a purine base (i.e., a purin-9-yl group) or a pyrimidine base (i.e., a 2-oxo-1,2-dihydropyrimidin-1-yl group), for example. These bases may have any one or more substituents selected from the α group consisting of a hydroxy group, linear alkyl groups having 1 to 6 carbon atoms, linear alkoxy groups having 1 to 6 carbon atoms, a mercapto group, linear alkylthio groups having 1 to 6 carbon atoms, an amino group, linear alkylamino groups having 1 to 6 carbon atoms, and halogen atoms.

Specific examples of the "Base" above include an adeninyl group, a guaninyl group, a cytosinyl group, an uracinyl group, a thyminyl group, a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, and a 4-amino-5-methyl-2-oxo-1,2-dihydropyrimidin-1-yl group.

Alternatively, from the viewpoint of introducing "Bases" into an oligonucleotide therapeutic, the "Bases" are preferably groups represented by structural formulae below:

[Chemical Formula 10]

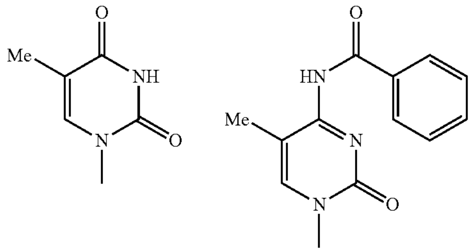

-continued

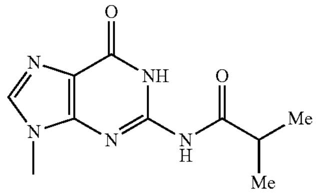
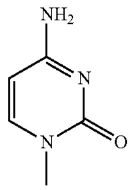
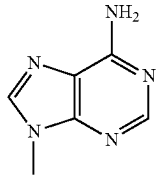
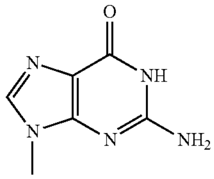
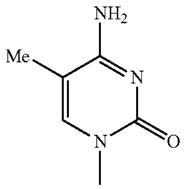
or
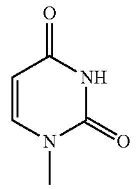

as well as a 2-oxo-4-hydroxy-5-methyl-1,2-dihydropyrimidin-1-yl group, a 2-oxo-4-amino-1,2-dihydropyrimidin-1-yl group, a 6-aminopurin-9-yl group, a 2-amino-6-hydroxypurin-9-yl group, a 4-amino-5-methyl-2-oxo-1,2-dihydropyrimidin-1-yl group, and a 2-oxo-4-hydroxy-1,2-dihydropyrimidin-1-yl group are favorable. It is preferable that a hydroxy group and an amino group included in the above-mentioned groups serving as "Bases" are protected by a protecting group during oligonucleotide synthesis.

Here, in one embodiment, examples of the compound represented by the formula (I) include compounds represented by the following formulae (I-1) to (I-6):

[Chemical Formula 11]

(I-1)

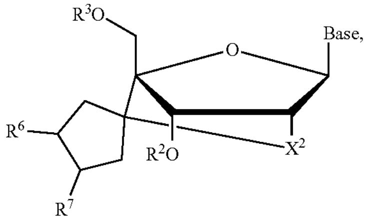

(I-2)

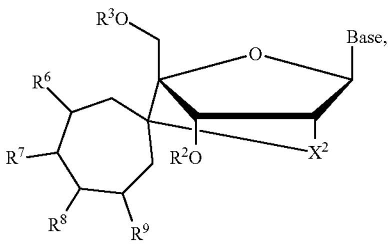

-continued (I-3)

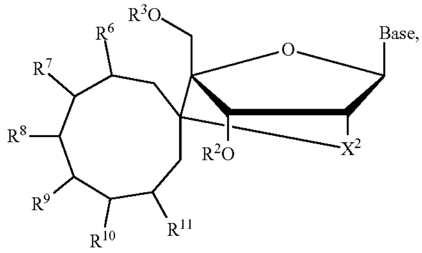

and (I-4)

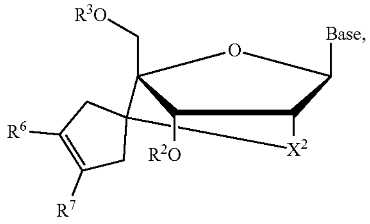

(I-5)

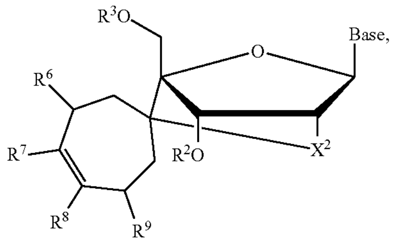

(I-6)

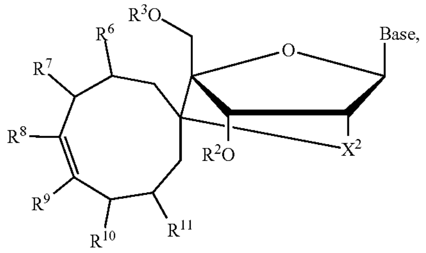

where Base, $R^2$, $R^3$, and $X^2$ are as defined for the formula (I) above, and $R^6$, $R^7$, $R^8$, $R^9$, $R^{10}$, and $R^{11}$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms. Here, $R^6$ and $R^7$ in the formulae (I-1) and (I-4) above are both hydrogen atoms. Alternatively, $R^6$, $R^7$, $R^8$, and $R^9$ in the formulae (I-2) and (I-5) above are all hydrogen atoms. Alternatively, $R^6$, $R^7$, and $R^8$, and $R^9$, $R^{10}$, and $R^{11}$ in the formulae (I-3) and (I-6) above are all hydrogen atoms.

Alternatively, in one embodiment, other examples of the compound represented by the formula (I) include compounds represented by the following formula (I'):

[Chemical Formula 12]

(I')

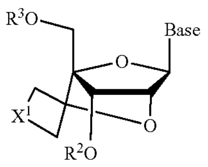

where Base, $R^2$, $R^3$, and $X^1$ are as defined for the formula (I) above.

Alternatively, in one embodiment, other examples of the compound represented by the formula (I) include compounds represented by the following formulae (I-1) and (I-4):

[Chemical Formula 13]

(I-1)

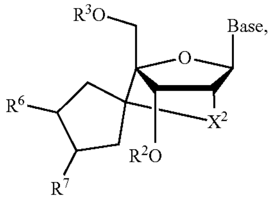

and (I-4)

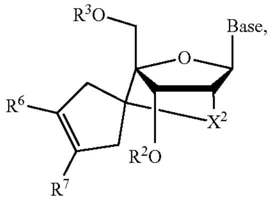

where Base, $R^2$, $R^3$, and $X^2$ are as defined for the formula (I) above, and $R^6$ and $R^7$ are each independently a hydrogen atom, a linear alkyl group having 1 to 3 carbon atoms, —$NHR^{4b}$), where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms. Here, $R^6$ and $R^7$ in the formulae (I-1) and (I-4) above are both hydrogen atoms.

Alternatively, in one embodiment, yet other examples of the compound represented by the formula (I) include compounds represented by the following formulae (I'-1) and (I'-4):

[Chemical Formula 14]

(I'-1)

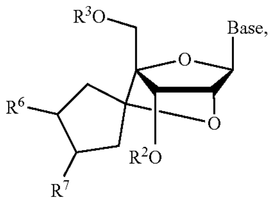

and

-continued (I'-4)

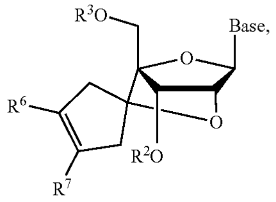

where Base, $R^2$, and $R^3$ are as defined for the formula (I) above, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms. Here, $R^6$ and $R^7$ in the formulae (I'-1) and (I'-4) above are both hydrogen atoms, for example.

In a bridged nucleoside according to the present invention, a cyclic substituent is introduced at the 6' position in the formula (I) as described above. With such a structure, the nucleoside of the present invention does not have an isomeric structure at the 6' position, and therefore, the separation of isomers during synthesis is no longer necessary. Also, the bridged nucleoside of the present invention can improve the nuclease-resistant ability of an oligonucleotide, which will be described later, due to the cyclic substituent introduced at the 6' position in the formula (I). Furthermore, ring strain of such substituents directly affects the conformation of the sugar moiety. Therefore, the bridged nucleoside of the present invention can further improve binding affinity of an oligonucleotide obtained using the nucleotide for ssRNA

Oligonucleotide

In the present invention, an oligonucleotide can be easily produced by using such a bridged nucleoside represented by the formula (I), and using, for example, an amidite method that is well known in the art, or triphosphorylation such as that described in M. Kuwahara et al., Nucleic Acids Res., 2008, Vol. 36, No. 13, pp. 4257-4265.

An oligonucleotide of the present invention or a pharmacologically acceptable salt thereof (these may be collectively referred to as "oligonucleotides of the present invention" hereinafter) contains at least one nucleoside structure represented by a formula (II) below:

[Chemical Formula 15]

(II)

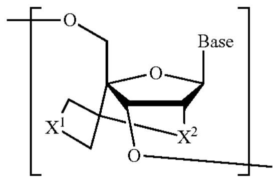

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, $X^1$ is an alkylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms, or an alkenylene group having 2 to 8 carbon atoms that may have undergone substitution by a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms, and $X^2$ is an oxygen atom, a sulfur atom, —NH—, —$N(CH_3)$—, or a methylene group.

In one embodiment, examples of the nucleoside structure represented by the formula (II) contained in the oligonucleotides of the present invention include structures represented by the following formulae (II-1) to (II-6):

[Chemical Formula 16]

(II-1)

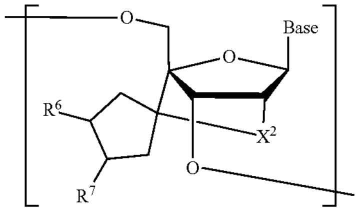

, (II-2)

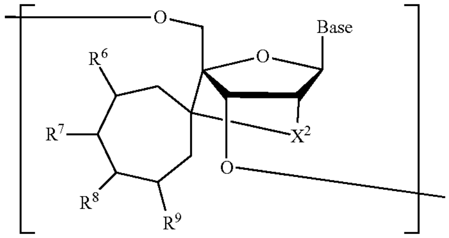

, (II-3)

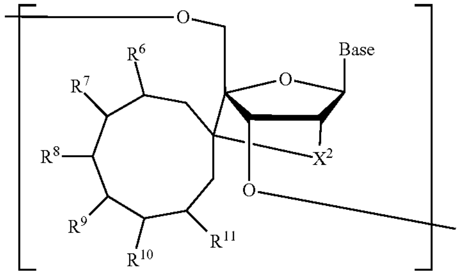

, and

-continued (II-4)

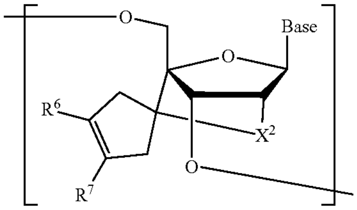

, (II-5)

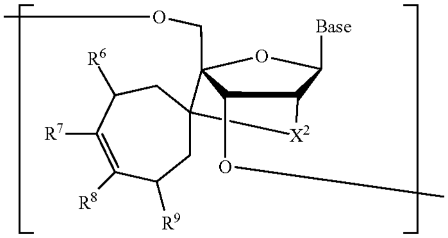

, (II-6)

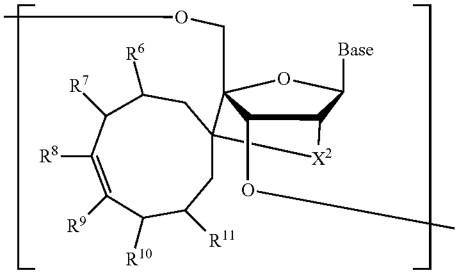

where Base and $X^2$ are as defined for the formula (II) above, and $R^6$, $R^7$, $R^8$, $R^9$, $R^{10}$, and $R^{11}$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms. Here, $R^6$ and $R^7$ in the formulae (II-1) and (II-4) above are both hydrogen atoms, for example. Alternatively, $R^6$, $R^7$, $R^8$, and $R^9$ in the formulae (II-2) and (II-5) above are all hydrogen atoms. Alternatively, $R^6$, $R^7$, and $R^8$, and $R^9$, $R^{10}$, and $R^{11}$ in the formulae (II-3) and (II-6) above are all hydrogen atoms.

Alternatively, in one embodiment, other examples of the nucleoside structure represented by the formula (II) contained in the oligonucleotides of the present invention include structures represented by the following formula (II'):

[Chemical Formula 17]

(II')

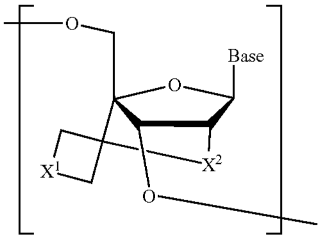

where Base and $X^1$ are as defined for the formula (II) above.

Alternatively, in one embodiment, other examples of the nucleoside structure represented by the formula (II) contained in the oligonucleotides of the present invention include structures represented by the following formulae (II-1) and (II-4):

[Chemical Formula 18]

(II-1)

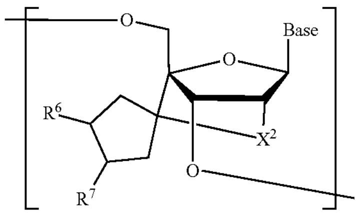

, and (II-4)

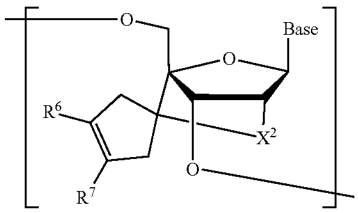

where Base and $X^2$ are as defined for the formula (II) above, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms. Here, $R^6$ and $R^7$ in the formulae (II-1) and (II-4) above are both hydrogen atoms, for example.

Alternatively, in one embodiment, other examples of the nucleoside structure represented by the formula (II) contained in the oligonucleotides of the present invention include structures represented by the following formulae (II'-1) and (II'-4):

[Chemical Formula 19]

(II'-1)

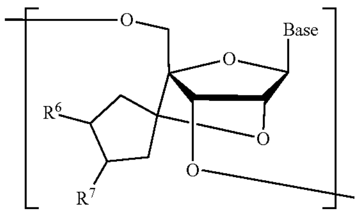

, and (II'-4)

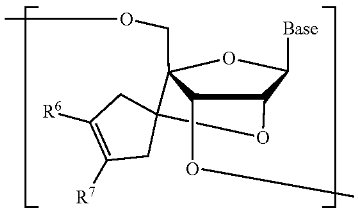

where Base is as defined for the formula (II) above, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms. Here, $R^6$ and $R^7$ in the formulae (II'-1) and (II'-4) above are both hydrogen atoms, for example.

The oligonucleotide of the present invention has at least one nucleoside structure at any position. There is no particular limitation on the positions and number of the nucleoside structures, and the oligonucleotide can be designed as appropriate depending on the purpose.

An oligonucleotide (antisense molecule) containing such a nucleoside structure has significantly improved nuclease-resistant ability when compared with the cases where conventional 2',4'-BNA/LNA is used, and also has good binding affinity for ssRNA comparable to that of known 2',4'-BNA/LNA.

With all these facts, the oligonucleotide of the present invention synthesized using the bridged nucleoside of the present invention is expected to be useful as a pharmaceutical agent (antisense molecule), such as antitumor agents and antiviral drugs, inhibiting the functions of specific genes to treat a disease.

In particular, for antisense therapies, the binding affinity for complementary sense strand RNAs and the resistance to in vivo DNA-degrading enzymes are both required. Generally, a nucleic acid in the form of a single strand constantly has a structural fluctuation of a sugar moiety between the form close to a sugar moiety in a double-stranded DNA and the form close to a sugar moiety in a double-stranded DNA-RNA or a double-stranded RNA. The binding affinity for target ssRNA can be improved by immobilizing the fluctuation on the conformation during double strand formation in advance. Also, a nucleic acid degrading enzyme cleaves phosphodiester moieties of oligonucleic acid. However, the degradation of oligonucleic acid can be suppressed through steric hindrance by introducing a bulky substituent into the sugar moiety or the like.

As described above, a bridged nucleoside of the present invention has a bulky cyclic substituent at the 6' position. Therefore, an oligonucleotide obtained using this bridged nucleoside can improve the above binding affinity for ssRNA and have great enzyme-resistant ability.

Additives typically used in the art of pharmaceuticals such as excipients, binders, preservatives, oxidation stabilizers, disintegrants, lubricants, and flavoring substances can be added to the oligonucleotide of the present invention to prepare parenteral formulations or liposomal formulations. Also, for example, topical formulations such as liquids, creams, and ointments may be prepared by adding pharmaceutical carriers typically used in the art.

EXAMPLES

Hereinafter, the present invention will be described in greater detail using examples. However, the present invention is not limited to the examples below.

Example 1: Synthesis of Bridged Nucleoside (1)

[Chemical Formula 20]

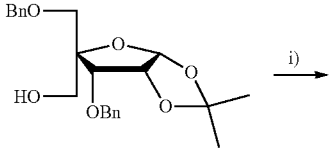

1

-continued
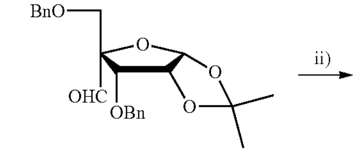
2
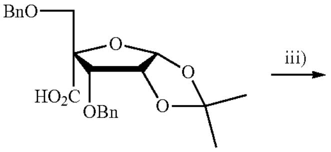
3
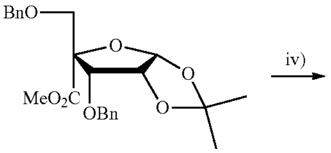
4
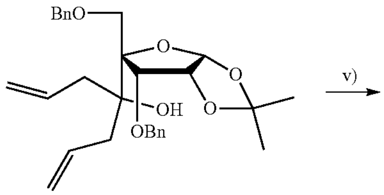
5
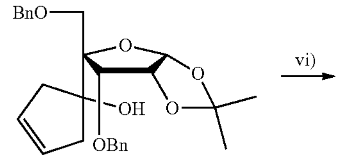
6
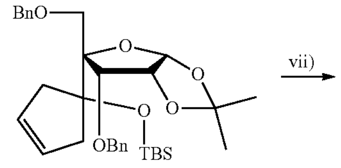
7
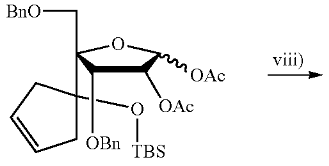
8
-continued
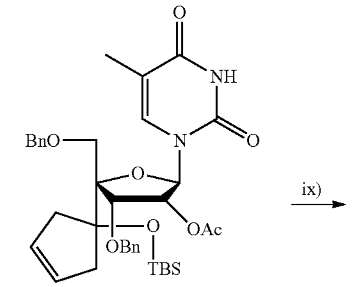
9
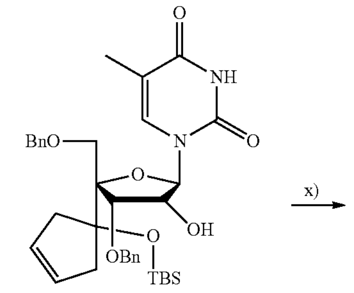
10
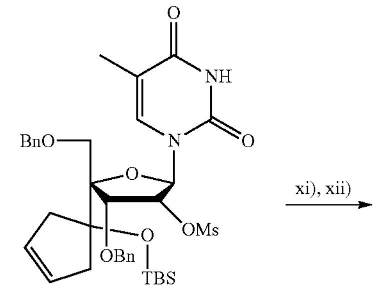
11
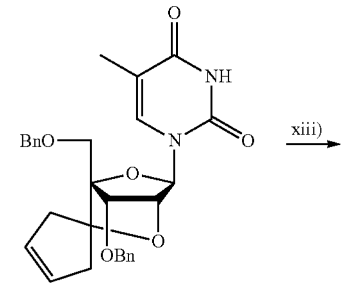
12
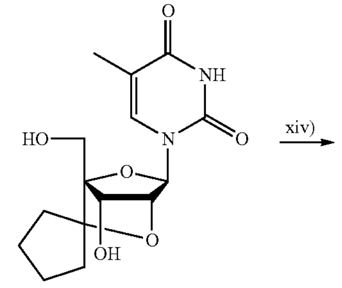
13

-continued

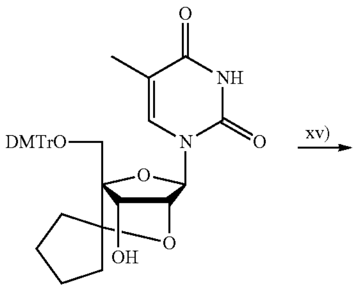

14

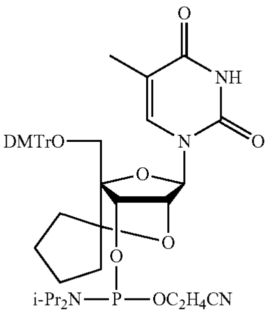

15

Reagents and Conditions for Each Step: (i) DMP, $CH_2Cl_2$, 0° C. to rt, 1 h, 94%; (ii) $H_2O_2$ aq., $NaH_2PO_4$ aq., $NaClO_2$ aq., MeCN, 0° C. to rt, 2 h, quant.; (iii) MeI, $NaHCO_3$, DMF, rt, 22 h, 98%; (iv) Allyl Magnesiumbromide, $CeCl_3$, THF, rt, 14 h, 98%; (v) Glubss 2nd. catalyst, $CH_2Cl_2$, reflux, 4 h, 90%; (vi) TBSOTf, 2,6-lutidine, $CH_2Cl_2$, rt, 20 h, 94%; (vii) TFA, $AcO_2$, AcOH, rt, 2 h, 86%; (viii) Thymine, TMSOTf, BSA, MeCN, reflux, 3 h, 89%; (ix) $K_2CO_3$, MeOH, rt, 5 h, 97%; (x) MsCl, pyridine, rt, 5 h, quant.; (xi) TBAF, THF, rt, 30 h; (xii) $K_2CO_3$, DMF, 90° C., 20 h, (83% in 2 steps); (xiii) $H_2$, $Pd(OH)_2$/C, AcOEt, rt, 0.5 h, 80% (xiv) DMTrCl, pyridine, rt, 8 h, quant.; (xv) 2-cyanoethyl-N,N-diisopropylchlorophosphoramidite, DIPEA, $CH_2Cl_2$, rt, 8 h, 58%.

(1-1) Synthesis of Compound 5

[Chemical Formula 21]

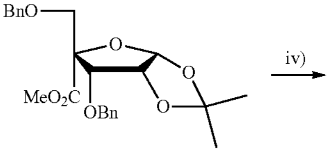

4

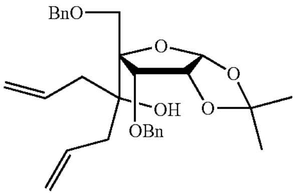

5

In an argon atmosphere, allylmagnesium bromide (33 mL, 33.0 mmol) was added at room temperature to an anhydrous tetrahydrofuran solution (60 mL) of a compound 4 (3.69 g, 8.61 mmol) produced through three steps i) to iii) from a compound 1 using the method described in "Yamaguchi, T. et al., Chem. Commun., 2015, No. 51, pp. 9737-9740" and anhydrous cerium (III) chloride (7.99 g, 32.4 mmol), and the resulting mixture was stirred for 14 hours. After completion of the reaction, an aqueous solution of ammonium chloride was added to concentrate an organic layer. Then, filtration was performed using cerite, and filtrate was extracted using ethyl acetate. The obtained residue was purified through silica gel column chromatography ($SiO_2$, hexane ethyl acetate=from 32:1 to 6:1) to obtain a compound 5 (4.06 g, 98%) as a colorless and transparent oily substance.

Table 1 shows data on the properties of the obtained compound 5.

TABLE 1

| Physical property data of the obtained compound 5 |
|---|
| $^1$H NMR (300 MHz, $CDCl_3$) δ 7.24-7.29 (m, 10H), 5.84-5.98 (m, 3H), 4.88-5.00 (m, 4H), 4.85 (d, J = 10.7 Hz, 1H), 4.78 (dd, J = 4.1, 5.5 Hz, 1H), 4.53 (d, J = 12.0 Hz, 1H), 4.42 (d, J = 11.7 Hz, 1H), 4.37-4.41 (m, 2H), 4.02 (bs, 1H), 3.66 (d, J = 9.6 Hz, 1H), 3.58 (d, J = 9.3 Hz, 1H), 2.76 (dd, J = 5.8, 14.4 Hz, 1H), 2.41-2.52 (m, 2H), 2.28 (dd, J = 7.6, 14.4 Hz, 1H), 1.61 (s, 3H), 1.39 (s, 3H); $^{13}$C NMR (76 MHz, $CDCl_3$) δ 137.8, 136.9, 134.9, 134.7, 128.5, 128.2, 128.1, 127.8, 127.5, 117.1, 114.7, 105.9, 92.7, 81.7, 80.9, 74.6, 73.7, 73.5, 41.2, 40.6, 27.7, 27.2; HRMS (MALDI) Calculated for $C_{29}H_{36}O_6Na$ $[M + Na]^+$: 503.2404, Found 503.2404. |

(1-2) Synthesis of Compound 6

[Chemical Formula 22]

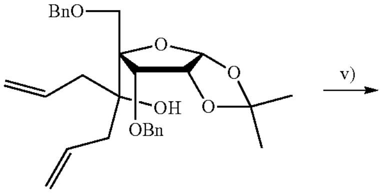

5

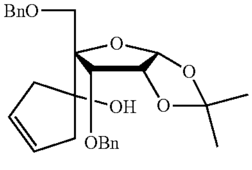

6

In an argon atmosphere, a second-generation Grubbs catalyst (425 mg, 0.501 mmol) was added at room temperature to an anhydrous dichloromethane solution (110 mL) of the compound 5 (1.60 g, 3.54 mmol) obtained above, and the resulting mixture was heated under reflux for 4 hours. After completion of the reaction, the mixture was concentrated, and the obtained residue was purified through silica gel column chromatography ($SiO_2$, hexane ethyl acetate=from 32:1 to 10:1) to obtain a compound 6 (1.35 g, 90%) as a pale yellow viscous oily substance.

Table 2 shows data on the properties of the obtained compound 6.

TABLE 2

| Physical property data of the obtained compound 6 |
|---|
| $^1$H NMR (300 MHz, $CDCl_3$) δ 7.28-7.36 (m, 10H), 5.92 (d, J = 3.5 Hz, 1H), 5.58-5.65 (m, 2H), 4.87 (d, J = 11.3 Hz, 1H), 4.77 (dd, J = 4.1, 8.6 Hz, 1H), 4.54 (d, J = 12.0 Hz, 1H), 4.38-4.47 (m, 3H), 3.75 (bs, 1H), 3.53 (d, J = 9.6 Hz, 1H), 3.16 (m, 2H), 2.62-2.81 (m, 1H), 2.34-2.45 (m, 1H), 2.29 (d, J = 16.8 Hz, 1H), 1.63 (s, 3H), 1.38 (s, 3H); $^{13}$C NMR (76 MHz, $CDCl_3$) δ 138.0, 137.9, 137.2, 128.5, 128.4, 128.1, 127.4, 127.0, 114.6, 105.7, 92.1, 83.0, 80.8, 80.5, 75.1, 73.7, 73.4, 45.1, 27.3, 27.1; HRMS (MALDI) Calculated for $C_{27}H_{32}O_6Na$ $[M + Na]^+$: 475.2091, Found 475.2091. |

(1-3) Synthesis of Compound 7

[Chemical Formula 23]

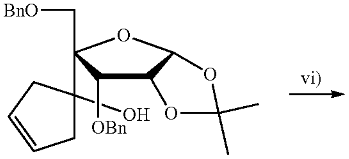

6

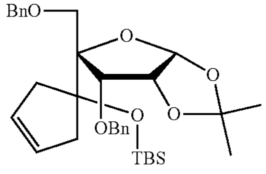

7

In an argon atmosphere, 2,6-lutidine (2.20 mL, 19.0 mmol) and tert-butyldimethylsilyl trifluoromethanesulfonic acid (3.00 mL, 13.1 mmol) were added at 0° C. to an anhydrous dichloromethane solution (31 mL) of the compound 6 (1.21 g, 2.67 mmol) obtained above, and the resulting mixture was stirred at room temperature for 20 hours. After completion of the reaction, a saturated aqueous solution of sodium hydrogen carbonate was added, and an organic layer was extracted using ethyl acetate. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, hexane: ethyl acetate=from 10:0 to 9:1) to obtain a compound 7 (1.43 g, 94%) as a colorless and transparent viscous oily substance.

Table 3 shows data on the properties of the obtained compound 7.

TABLE 3

| Physical property data of the obtained compound 7 |
|---|
| $^1$H NMR (300 MHz, $CDCl_3$) δ 7.26-7.40 (m, 10H), 5.93 (d, J = 4.5 Hz, 1H), 5.60-5.63 (m, 2H), 4.88 (dd, J = 4.8, 5.9 Hz, 1H), 4.78 (d, J = 11.0 Hz, 1H), 4.58 (d, J = 11.7 Hz, 1H), 4.45 (d, J = 12.0 Hz, 1H), 4.38 (d, J = 11.0 Hz, 1H), 4.14 (d, J = 5.8 Hz, 1H), 3.89 (d, J = 8.2 Hz, 1H), 3.61 (d, J = 9.3 Hz, 1H), 2.88-3.15 (m, 2H), 2.39-2.70 (m, 1H), 2.20 (d, J = 16.8 Hz, 1H), 1.51 (s, 3H), 1.36 (s, 3H), 0.76 (s, 9H), −0.04 (s, 3H), −0.14 (s, 3H); $^{13}$C NMR (76 MHz, $CDCl_3$) δ 138.5, 138.1, 128.5, 127.9, 127.7, 127.5, 127.1, 114.3, 105.6, 86.4, 82.5, 80.5, 73.8, 73.6, 45.5, 44.2, 28.0, 27.4, 26.0, 18.3, −3.46, −3.56; HRMS (MALDI) Calculated for $C_{33}H_{46}O_6NaSi$ $[M + Na]^+$: 589.2956, Found 589.2956. |

(1-4) Synthesis of Compound 8

[Chemical Formula 24]

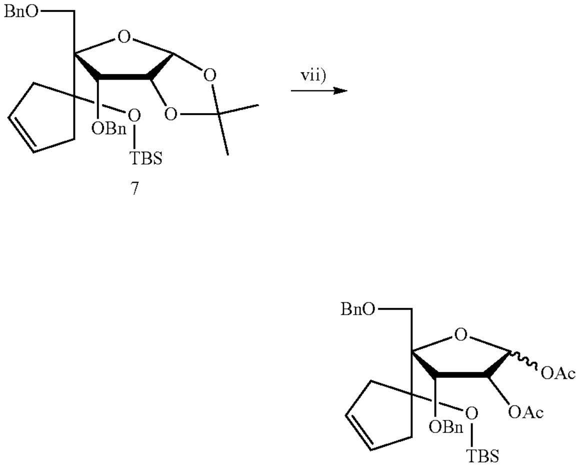

7

8

In an argon atmosphere, acetic anhydride (3.05 mL, 32.3 mmol) and trifluoro acetate (295 μL, 3.86 mmol) were added at 0° C. to an acetic acid solution (1.85 mL, 32.3 mmol) of the compound 7 (911 mg, 1.61 mmol) obtained above, and the resulting mixture was stirred at room temperature for 2 hours. After completion of the reaction, a saturated aqueous solution of sodium hydrogen carbonate was added, and an organic layer was extracted using ethyl acetate. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, hexane: ethyl acetate=from 9:1 to 4:1) to obtain a compound 8 (841 mg, 86%) as a colorless and transparent viscous oily substance.

Table 4 shows data on the properties of the obtained compound 8.

TABLE 4

| Physical property data of the obtained compound 8 |
|---|
| $^1$H NMR (300 HMz, $CDCl_3$) δ 7.26-7.43 (m, 10H), 6.49 (d, J = 5.1 Hz, 1/2H), 6.35 (d, J = 5.1 Hz, 1/2H), 5.67-5.71 (m, 3/2H), 5.50-5.64 (m, 3/2H), 4.62-4.74 (m, 2H), 4.32-4.56 (m, 3H), 4.00 (d, J = 10.0 Hz, 1/2H), 3.97 (d, J = 12.0 Hz, 1/2H), 3.59 (d, J = 6.9 Hz, 1/2H), 3.57 (d, J = 6.9 Hz, 1/2H), 2.82-3.18 (m, 2H), 2.44 (d, J = 18.2 Hz, 1H), 2.16-2.25 (m, 1H), 2.11 (s, 3/2H), 2.04 (s, 3/2H), 1.89 (s, 3/2H), 1.84 (s, 3/2H), 0.79 (s, 9/2H), 0.78 (s, 9/2H), −0.01 (s, 3/2H), −0.03 (s, 3/2H), −0.10 (s, 3/2H), −0.13 (s, 3/2H); HRMS (MALDI) Calculated for $C_{34}H_{46}O_8NaSi$ $[M + Na]^+$: 633.2854, Found 633.2851. |

(1-5) Synthesis of Compound 9

[Chemical Formula 25]

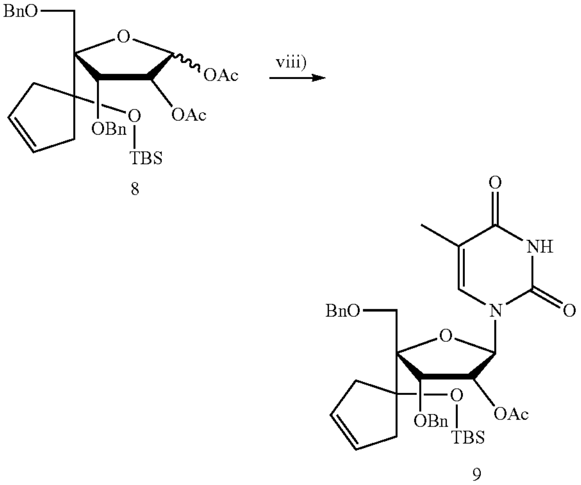

8

9

In an argon atmosphere, thymine (242 mg, 1.91 mmol) and N,O-bis-trimethylsilylacetamide (780 μL, 3.18 mmol) were successively added at room temperature to an anhydrous acetonitrile solution (5.6 mL) of the compound 8 (389 mg, 0.637 mmol) obtained above, and the resulting mixture was stirred at room temperature for 1 hour. Then, in an argon atmosphere, trimethylsilyl trifluoromethanesulfonic acid (175 μl, 0.969 mmol) was added thereto at 0° C., and the resulting mixture was heated under reflux for 5 hours. After completion of the reaction, a saturated aqueous solution of sodium hydrogen carbonate was added, and an organic layer was extracted using ethyl acetate. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, hexane:ethyl acetate=from 9:1 to 4:1) to obtain a compound 9 (385 mg, 89%) as a white solid.

Table 5 shows data on the properties of the obtained compound 9.

TABLE 5

| Physical property data of the obtained compound 9 |
| --- |
| $^1$H NMR (300 MHz, $CDCl_3$) δ 8.33 (s, 1H), 7.66 (d, J = 1.0 Hz, 1H), 7.27-7.46 (m, 10H), 6.42 (d, J = 8.9 Hz, 1H), 5.57-5.65 (m, 3H), 4.79 (d, J = 11.3 Hz, 1H), 4.70 (d, J = 11.7 Hz, 1H), 4.64 (d, J = 11.7 Hz, 1H), 4.49 (d, J = 11.3 Hz, 1H), 4.44 (d, J = 5.1 Hz, 1H), 4.06 (d, J = 9.6 Hz, 1H), 3.76 (d, J = 10.0 Hz, 1H), 2.83 (d, J = 16.8 Hz, 2H), 2.57 (d, J = 17.9 Hz, 1H), 2.22 (d, J = 16.1 Hz, 1H), 1.90 (s, 3H), 1.59 (s, 3H), 0.80 (s, 9H), −0.01 (s, 3H), −0.13 (s, 3H); $^{13}$C NMR (76 MHz, $CDCl_3$) δ 170.7, 163.4, 150.7, 138.1, 137.1, 136.0, 129.2, 128.8, 128.3, 128.2, 127.7, 127.5, 127.3, 127.0, 111.5, 91.3, 87.4, 84.6, 81.3, 75.5, 75.0, 73.9, 73.8, 44.9, 44.5, 26.3, 20.6, 18.4, 12.2, −3.39, −3.44; HRMS (MALDI) Calculated for $C_{37}H_{48}N_2O_8NaSi$ $[M + Na]^+$: 699.3072, Found 699.3069. |

(1-6) Synthesis of Compound 10

[Chemical Formula 26]

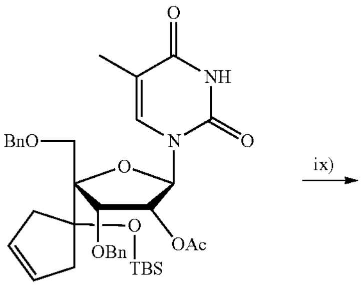

9

-continued

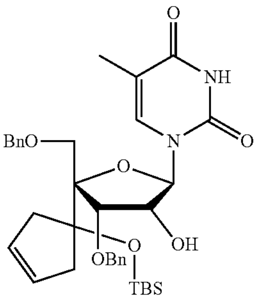

10

In an argon atmosphere, potassium carbonate (607 mg, 4.39 mmol) was added at 0° C. to a methanol solution (14.6 mL) of the compound 9 (986 mg, 1.46 mmol) obtained above, and the resulting mixture was stirred at room temperature for 5 hours. After completion of the reaction, a saturated aqueous solution of sodium hydrogen carbonate was added, and an organic layer was extracted using diethyl ether. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, hexane:ethyl acetate=from 4:1 to 1:1) to obtain a compound 10 (895 mg, 97%) as a white solid.

Table 6 shows data on the properties of the obtained compound 10.

TABLE 6

| Physical property data of the obtained compound 10 |
| --- |
| $^1$H NMR (300 MHz, $CDCl_3$) δ 8.32 (s, 1H), 7.58 (s, 1H), 7.26-7.41 (m, 10H), 5.99 (d, J = 8.2 Hz, 1H), 5.63-5.69 (m, 2H), 5.00 (d, J = 10.3 Hz, 1H), 4.66 (d, J = 11.7 Hz, 1H), 4.58 (d, J = 11.7 Hz, 1H), 4.57 (d, J = 11.0 Hz, 2H), 4.22 (d, J = 5.5 Hz, 1H), 4.06 (d, J = 8.6 Hz, 1H), 3.73 (d, J = 9.6 Hz, 1H), 2.60-2.87 (m, 4H), 2.24 (d, J = 16.8 Hz, 1H), 1.63 (s, 3H), 0.82 (s, 9H), 0.04 (s, 3H), −0.03 (s, 3H); $^{13}$C NMR (76 MHz, $CDCl_3$) δ 163.3, 150.9, 147.3, 144.8, 137.2, 137.0, 136.0, 128.9, 128.8, 128.7, 128.2, 128.1, 127.6, 111.3, 90.7, 87.6, 83.2, 75.9, 75.0, 74.0, 44.7, 44.6, 26.3, 18.5, 12.2, −3.18, −3.31; HRMS (MALDI) Calculated for $C_{35}H_{46}N_2O_7NaSi$ $[M + Na]^+$: 657.2966, Found 657.2963. |

(1-7) Synthesis of Compound 11

[Chemical Formula 27]

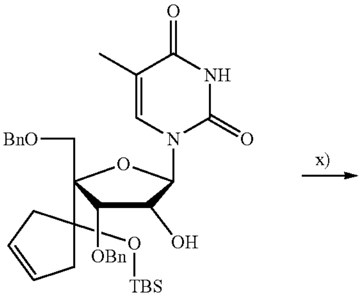

10

-continued

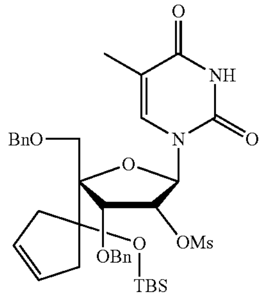

11

-continued

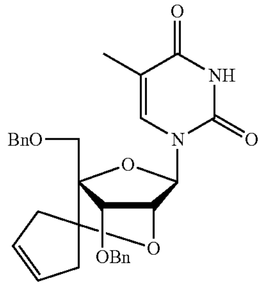

12

In an argon atmosphere, methanesulfonic acid chloride (170 μL, 2.19 mmol) was added at 0° C. to a dehydrated pyridine solution (14.5 mL) of the compound 10 (895 mg, 1.41 mmol) obtained above, and the resulting mixture was stirred at room temperature for 4 hours. After completion of the reaction, water was added, and an organic layer was extracted using ethyl acetate. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, hexane:ethyl acetate=from 9:1 to 4:1) to obtain a compound 11 (992 mg, quantitative) as a white solid.

Table 7 shows data on the properties of the obtained compound 11.

TABLE 7

| Physical property data of the obtained compound 11 |
|---|
| $^1$H NMR (300 MHz, $CDCl_3$) δ 8.52 (s, 1H), 7.58 (s, 1H), 7.29-7.42 (m, 10H), 6.40 (d, J = 8.3 Hz, 1H), 5.67 (d, J = 8.3 Hz, 1H), 5.65 (d, J = 8.2 Hz, 1H), 5.58 (d, J = 5.5 Hz, 1H), 4.80 (d, J = 11.0 Hz, 1H), 4.76 (d, J = 11.3 Hz, 1H), 4.69 (d, J = 11.3 Hz, 1H), 4.64 (d, J = 11.7 Hz, 1H), 4.36 (d, J = 5.2 Hz, 1H), 4.04 (d, J = 10.0 Hz, 1H), 3.78 (d, J = 9.6 Hz, 1H), 2.84 (s, 3H), 2.76-2.82 (m, 2H), 2.58 (d, J = 17.9 Hz, 1H), 2.21 (d, J = 16.8 Hz, 1H), 1.59 (s, 3H), 0.81 (s, 9H), −0.01 (s, 3H), −0.12 (s, 3H); $^{13}$C NMR (76 MHz, $CDCl_3$) δ 163.3, 150.7, 137.8, 136.7, 135.3, 129.2, 128.9, 128.3, 127.7, 127.5, 127.2, 111.9, 91.2, 87.2, 84.3, 81.3, 75.0, 74.0, 73.5, 44.7, 44.4, 38.0, 26.2, 18.3, 12.2, −3.44, −3.50; HRMS (MALDI) Calculated for $C_{36}H_{48}N_2O_9NaSiS$ $[M + Na]^+$: 735.2742, Found 735.2718. |

(1-8) Synthesis of Compound 12

[Chemical Formula 28]

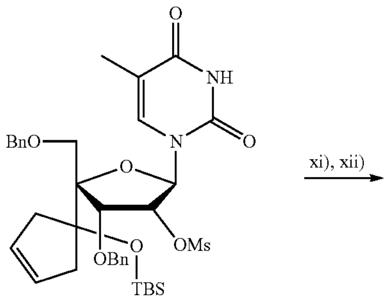

11

In an argon atmosphere, a tetrahydrofuran solution (4.18 mL, 4.18 mmol) of tetrabutylammonium fluoride was added at 0° C. to a dehydrated tetrahydrofuran solution (13.9 mL) of the compound 11 (992 mg, 1.39 mmol) obtained above, and the resulting mixture was stirred at room temperature for 30 hours. After completion of the reaction, water was added, and an organic layer was extracted using ethyl acetate. After the organic layer was washed with water and a saturated saline solution, the resulting organic layer was dried using anhydrous sodium sulfate, and the solvent was distilled away under reduced pressure. Potassium carbonate (577 mg, 4.17 mmol) was added at 0° C. to an N,N-dimethylformamide solution (13.9 mL) of the obtained residue without purifying the residue, and the resulting mixture was stirred at 90° C. for 20 hours. After completion of the reaction, water was added, and an organic layer was extracted using diethyl ether. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, hexane:ethyl acetate=from 4:1 to 1:2) to obtain a compound 12 (583 mg, 83% (two steps)) as a white solid.

Table 8 shows data on the properties of the obtained compound 12.

TABLE 8

| Physical property data of the obtained compound 12 |
|---|
| $^1$H NMR (300 MHz, $CDCl_3$) δ 8.47 (s, 1H), 7.55 (s, 1H), 7.25-7.33 (m, 10H), 5.63-5.67 (m, 2H), 5.55 (s, 1H), 4.65 (d, J = 11.3 Hz, 1H), 4.61 (s, 2H), 4.51 (d, J = 11.3 Hz, 1H), 4.51 (s, 1H), 4.05 (s, 1H), 3.87 (d, J = 11.0 Hz, 1H), 3.81 (d, J = 11.0 Hz, 1H), 2.94 (d, J = 18.2 Hz, 1H), 2.66 (s, 2H), 2.58 (d, J = 17.9 Hz, 1H), 1.57 (s, 3H); $^{13}$C NMR (76 MHz, $CDCl_3$) δ 163.8, 149.8, 137.5, 136.9, 135.1, 128.6, 128.5, 128.3, 128.1, 127.7, 127.6, 127.4, 110.0, 92.8, 88.5, 86.4, 73.9, 72.2, 64.9, 42.3, 41.5, 12.2; HRMS (MALDI) Calculated for $C_{29}H_{30}N_2O_6Na$ $[M + Na]^+$: 525.1996, Found 525.1997. |

(1-9) Synthesis of Compound 13

[Chemical Formula 29]

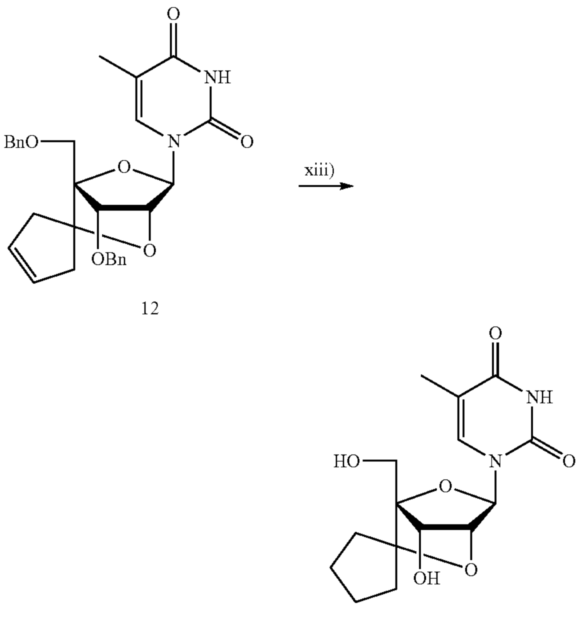

12

13

In a hydrogen gas atmosphere, 20% palladium hydroxide/carbon (44 mg, 40 parts by weight (with respect to the compound 12 (100 parts by weight)) was added at room temperature to an ethyl acetate solution (2.15 mL) of the compound 12 (110 mg, 0.219 mmol) obtained above, and the resulting mixture was stirred at room temperature for 0.5 hours while replacing the content in the flask with hydrogen gas several times. After completion of the reaction, filtration was performed, and filtrate was washed with ethyl acetate. Then, the solvent was distilled away under reduced pressure, and the obtained residue was purified using a PLC plate ($SiO_2$, chloroform:methanol=7:1) to obtain a compound 13 (57 mg, 80%) as a white solid.

Table 9 shows data on the properties of the obtained compound 13.

TABLE 9

| Physical property data of the obtained compound 13 |
|---|
| $^1$H NMR (300 MHz, $CD_3OD$) δ 7.78 (d, J = 1.4 Hz, 1H), 5.46 (s, 1H), 4.24 (s, 1H), 4.16 (s, 1H), 3.96 (d, J = 12.7 Hz, 1H), 3.88 (d, J = 12.7 Hz, 1H), 1.44-2.11 (m, 8H), 1.88 (d, J = 1.0 Hz, 3H); $^{13}$C NMR (76 MHz, $CD_3OD$) δ 168.8, 153.6, 137.0, 110.6, 95.5, 91.3, 87.7, 81.6, 72.4, 57.5, 36.8, 36.3, 26.5, 24.4, 13.0; HRMS (MALDI) Calculated for $C_{15}H_{20}N_2O_6Na$ $[M + Na]^+$: 347.1214, Found 347.1209. |

(1-10) Synthesis of Compound 14

[Chemical Formula 30]

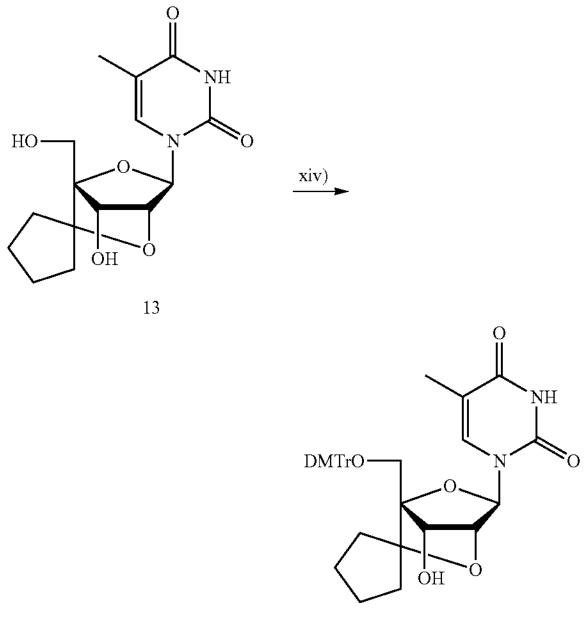

13

14

In an argon atmosphere, 4,4'-dimethoxytrityl chloride (320 mg, 0.944 mmol) was added at 0° C. to an anhydrous pyridine solution (5.3 mL) of the compound 13 (170 mg, 0.524 mmol) obtained above, and the resulting mixture was stirred at room temperature for 8 hours. After completion of the reaction, a saturated aqueous solution of sodium hydrogen carbonate was added, and an organic layer was extracted using ethyl acetate. After the organic layer was washed with water and a saturated saline solution, the resulting organic layer was dried using anhydrous sodium sulfate, and the solvent was distilled away under reduced pressure. The obtained residue was purified through silica gel column chromatography ($SiO_2$, 1% triethylamine-containing hexane:ethyl acetate=from 4:1 to 1:4) to obtain a compound 14 (329 mg, quantitative) as a white solid.

Table 10 shows data on the properties of the obtained compound 14.

TABLE 10

| Physical property data of the obtained compound 14 |
|---|
| $^1$H NMR (300 MHz, $CDCl_3$) δ 8.94 (s, 1H), 7.67 (s, 1H), 7.48 (d, J = 6.9 Hz, 2H), 7.24-7.49 (m, 7H), 6.86 (d, J = 8.6 Hz, 4H), 5.56 (s, 1H), 4.39 (s, 1H), 4.29 (d, J = 3.8 Hz, 1H), 3.80 (s, 6H), 3.56 (d, J = 11.0 Hz, 1H), 3.49 (d, J = 11.0 Hz, 1H), 2.37 (d, J = 6.2 Hz, 1H), 1.96-2.09 (m, 1H), 1.45-1.93 (m, 6H), 1.68 (s, 3H), 1.26-1.37 (m, 1H); $^{13}$C NMR (76 MHz, $CDCl_3$) δ 163.9, 158.6, 149.8, 144.4, 135.4, 135.3, 134.8, 130.0, 128.0, 127.1, 113.3, 110.2, 94.2, 89.6, 86.9, 86.2, 80.0, 73.0, 58.6, 55.2, 35.9, 35.8, 25.7, 23.4, 12.5; HRMS (MALDI) Calculated for $C_{36}H_{38}N_2O_8Na$ $[M + Na]^+$: 649.2520, Found 649.2526. |

(1-11) Synthesis of Compound 15

[Chemical Formula 31]

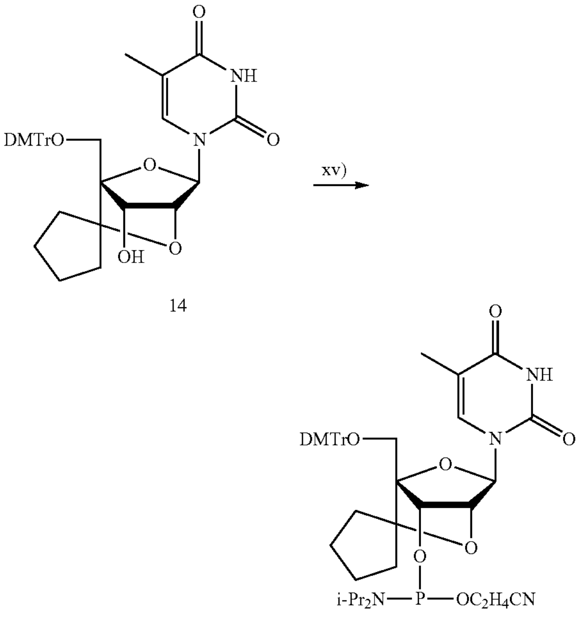

14

15

In an argon atmosphere, N,N-diisopropylethylamine (275 μL, 1.61 mmol) and 2-cyanoethyl-N,N-diisopropyl phosphorochloridate (175 μL, 0.784 mmol) were successively added at 0° C. to an anhydrous dichloromethane solution (5.3 mL) of the compound 14 (329 mg, 0.525 mmol) obtained above, and the resulting mixture was stirred at room temperature for 8 hours. After completion of the reaction, the solvent was distilled away under reduced pressure, and the obtained residue was purified through silica gel column chromatography ($SiO_2$, 1% triethylamine-containing hexane:ethyl acetate=from 4:1 to 2:1) and reprecipitation (toluene/hexane) to obtain a compound 15 (252 mg, 58%) as a white solid.

Table 11 shows data on the properties of the obtained compound 15.

TABLE 11

| Physical property data of the obtained compound 15 |
|---|
| $^1$H NMR (300 MHz, $CDCl_3$) δ 8.37 (s, 1H), 7.73 (s, 1H), 7.46 (d, J = 7.2 Hz, 2H), 7.24-7.37 (m, 7H), 6.82-6.88 (m, 4H), 5.89 (s, 1/2H), 5.58 (s, 1/2H), 4.52 (d, J = 7.9 Hz, 1H), 4.37 (dd, J = 9.3, 16.1 Hz, 1H), 3.81 (s, 6/2H), 3.80 (s, 6/2H), 3.46-3.54 (m, 4H), 2.54-2.78 (m, 1H), 2.37 (dd, J = 5.9, 12.0 Hz, 1H), 1.93-2.07 (m, 1H), 1.60-1.89 (m, 4H), 1.65 (s, 3/2H), 1.63 (s, 3/2H), 1.41-1.55 (m, 2H), 1.25-1.29 (m, 3H), 1.16 (d, J = 6.5 Hz, 3H), 1.12 (d, J = 6.9 Hz, 3H), 1.07 (d, J = 6.5 Hz, 3H), 0.98 (d, J = 6.5 Hz, 3H); $^{31}$P NMR (122 MHz, $CDCl_3$) δ 149.1, 148.7; HRMS (MALDI) Calculated for $C_{45}H_{55}N_4O_9NaP$ $[M + Na]^+$: 849.3599, Found 849.3658. |

The total yield of the compound 15 finally obtained through a series of synthetic pathways to obtain the compound 15 from the compound 1 was 22%. It was found that this value was a higher value than that of the total yield (18%) of the final product obtained through the synthetic pathway of the bridged nucleoside (scpBNA) described in Patent Document 1 and Non-Patent Document 5, for example, and the bridged nucleoside of this example was efficiently synthesized.

Example 2: Synthesis of Bridged Nucleoside (2)

[Chemical Formula 32]

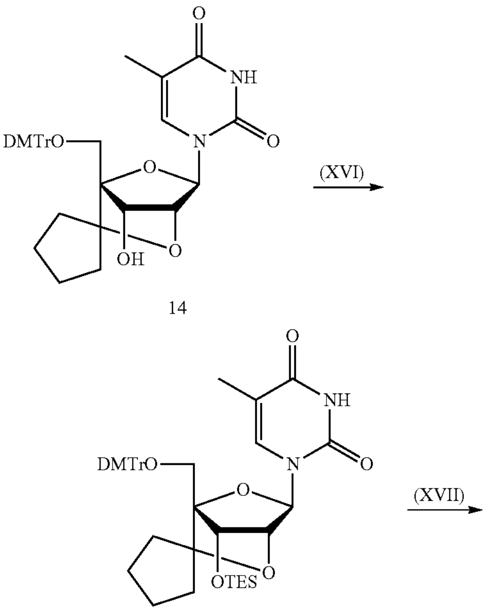

14

16

-continued

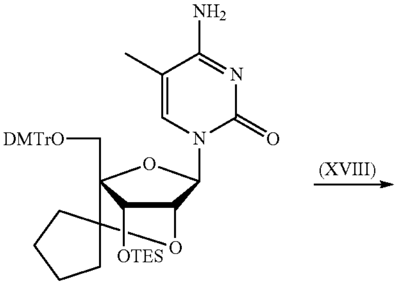

17

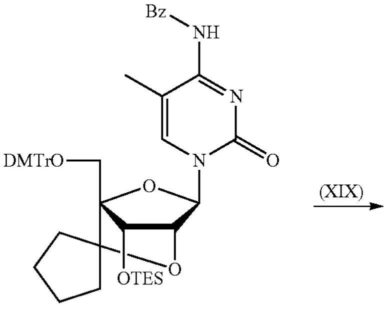

18

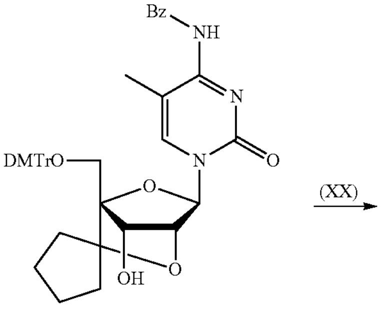

19

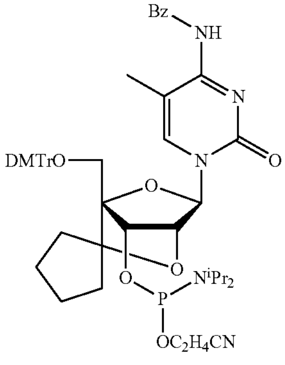

20

Reagents and Conditions for Each Step: (XVI) TESCl, pyridine, 0° C. to rt, 4 h, 72%; (XVII) 1,2,4-triazole, $POCl_3$, MeCN, 0° C. to rt, 50 min; $NH_3$ aq., 1,4-dioxane, rt, 1.5 h, 98% (2 steps); (XVIII) BzCl, pyridine, 0° C. to rt, 2.5 h, 62%; (XIX) TBAF, THF, 0° C. to rt, 20 min, quant; (XX) $(^iPr_2N)_2POC_2H_4CN$, DCI, $CH_2Cl_2$, rt, 2 h, 81%.

(2-1) Synthesis of Compound 16

[Chemical Formula 33]

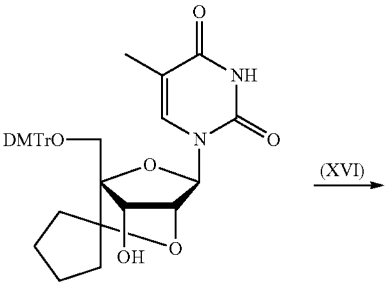

14

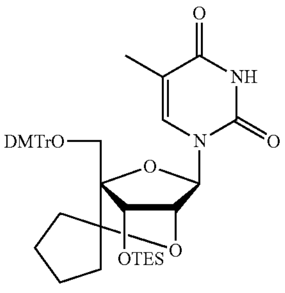

16

Under a nitrogen stream, chlorotriethylsilane (0.45 mL, 3.0 mmol) was added at 0° C. to an anhydrous pyridine solution (10 mL) of the compound 14 (626 mg, 999 μmol) obtained in Example 1 (1-10) above, and the resulting mixture was stirred at room temperature for 4 hours. After completion of the reaction, saturated aqueous sodium bicarbonate was added at 0° C., extraction was performed using ethyl acetate, and the extraction fraction was washed with water and a saturated saline solution. The resulting extraction fraction was dried using anhydrous sodium sulfate, and the solvent was then distilled away under reduced pressure. The obtained crude product was purified through silica gel column chromatography ($SiO_2$, n-hexane:ethyl acetate=1:1) to obtain a compound 16 (531 mg, 72%) as a white foam-like solid.

Table 12 shows data on the properties of the obtained compound 16.

TABLE 12

| Physical property data of the obtained compound 16 |
| --- |
| $^{1}H$ NMR (500 MHz, $CDCl_3$) δ 0.48-0.58 (m, 6H), 0.83-0.86 (m, 9H), 1.24-1.27 (m, 1H), 1.66 (s, 3H), 1.50-1.93 (m, 7H), 3.37 (d, J = 10.9 Hz, 1H), 3.44 (d, J = 10.9 Hz, 1H), 3.80 (s, 6H), 4.29 (s, 1H), 4.32 (s, 1H), 5.53 (s, 1H), 6.84 (d, J = 9.2 Hz, 2H), 6.84 (d, J = 9.2 Hz, 2H), 7.25-7.36 (m, 7H), 7.46 (d, J = 7.5 Hz, 2H), 7.79 (d, J = 1.2 Hz, 1H), 8.22 (s, 1H); $^{13}C$ NMR (125.8 MHz, $CDCl_3$) δ 4.7, 6.6, 12.6, 23.4, 25.5, 35.6, 35.8, 55.2, 58.5, 73.0, 80.0, 86.7, 86.8, 89.6, 94.5, 110.2, 113.2, 113.2, 127.1, 128.0, 128.1, 130.0, 130.1, 135.0, 135.3, 135.5, 144.4, 149.7, 158.7, 163.9; HRMS (MALDI) Calculated for $C_{42}H_{52}N_2O_8NaSi$ $[M + Na]^+$: 763.3391, Found 763.3369. |

(2-2) Synthesis of Compound 17

[Chemical Formula 34]

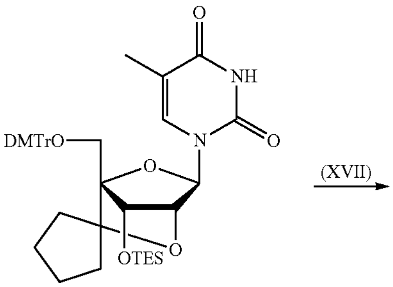

16

-continued

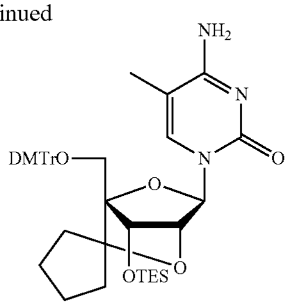

17

Under a nitrogen stream, phosphoryl chloride (136 μL, 1.5 mmol) was added dropwise at 0° C. to an anhydrous acetonitrile solution (4.8 mL) of the compound 16 (329 mg, 444 μmol) obtained above, triethylamine (1.1 mL, 8 mmol), and 1,2,4-triazole (537 mg, 7.8 mmol). The resulting mixture was stirred at room temperature for 1 hour, saturated aqueous sodium bicarbonate was added to a reaction solution, extraction was performed using ethyl acetate, and the extraction fraction was washed with water and a saturated saline solution. The resulting extraction fraction was dried using anhydrous sodium sulfate, and the solvent was then distilled away under reduced pressure. A 28 wt % aqueous solution of ammonia (500 μL, 7.3 mmol) was added at 0° C. to a 1,4-dioxane solution (2.0 mL) of the obtained residue, and the resulting mixture was stirred at room temperature for 1.5 hours. After completion of the reaction, the solvent was distilled away under reduced pressure. The obtained crude product was purified through silica gel column chromatography ($SiO_2$, chloroform:methanol=20:1) to obtain a compound 17 (322 mg, 98%, two steps) as a white foam-like solid.

Table 13 shows data on the properties of the obtained compound 17.

TABLE 13

| Physical property data of the obtained compound 17 |
| --- |
| $^{1}H$ NMR (500 MHz, $CDCl_3$) δ 0.45-0.55 (m, 6H), 0.81-0.84 (m, 9H), 1.22-1.26 (m, 1H), 1.43-1.92 (m, 7H), 1.68 (s, 3H), 3.36 (d, J = 10.9 Hz, 1H), 3.44 (d, J = 10.9 Hz, 1H), 3.80 (s, 6H), 4.30 (s, 1H), 4.38 (s, 1H), 5.60 (s, 1H), 6.84 (d, J = 8.9 Hz, 2H), 6.85 (d, J = 8.9 Hz, 2H), 7.22-7.38 (m, 7H), 7.48 (d, J = 7.5 Hz, 2H), 7.84 (s, 1H); $^{13}C$ NMR (125.8 MHz, $CDCl_3$) δ 4.7, 6.6, 13.2, 23.4, 25.6, 35.5, 35.8, 55.2, 58.7, 72.9, 80.0, 86.6, 87.3, 89.2, 94.2, 101.0, 113.1, 113.2, 127.0, 127.9, 128.1, 130.0, 130.1, 135.5, 135.6, 138.0, 144.6, 155.5, 158.6, 165.6; HRMS (MALDI) Calculated for $C_{42}H_{53}N_3O_7NaSi$ $[M + Na]^+$: 762.3550, Found762.3565. |

(2-3) Synthesis of Compound 18

[Chemical Formula 35]

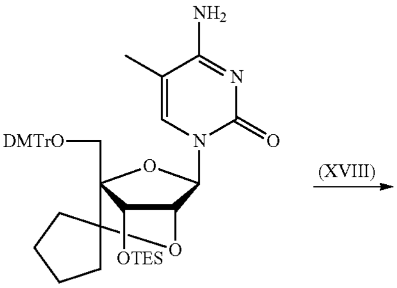

17

-continued

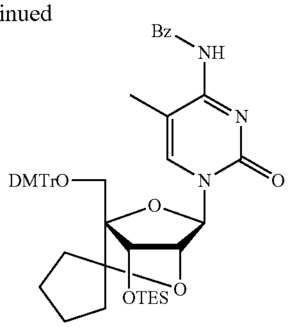

18

Under a nitrogen stream, benzoyl chloride (100 μL, 0.86 mmol) was added at 0° C. to an anhydrous pyridine solution (4.5 mL) of the compound 17 (322 mg, 0.435 mmol) obtained above, and the resulting mixture was stirred at room temperature for 2.5 hours. After completion of the reaction, saturated aqueous sodium bicarbonate was added, extraction was performed using ethyl acetate, and the extraction fraction was washed with water and a saturated saline solution. The resulting extraction fraction was dried using anhydrous sodium sulfate, and the solvent was then distilled away under reduced pressure. The obtained crude product was purified through silica gel column chromatography ($SiO_2$, n-hexane:ethyl acetate=5:1) to obtain a compound 18 (229 mg, 62%) as a white foam-like solid.

Table 14 shows data on the properties of the obtained compound 18.

TABLE 14

| Physical property data of the obtained compound 18 |
|---|
| $^1$H NMR (500 MHz, $CDCl_3$) δ 0.48-0.58 (m, 6H), 0.83-0.86 (m, 9H), 1.24-1.29 (m, 1H), 1.56 (s, 3H), 1.45-1.95 (m, 7H), 3.39 (d, J = 10.3 Hz, 1H), 3.47 (d, J = 10.9 Hz, 1H), 3.81 (s, 6H), 4.34 (s, 1H), 4.34 (s, 1H), 5.59 (s, 1H), 6.84-6.87 (m, 4H), 7.26-7.38 (m, 7H), 7.42-7.53 (m, 5H), 7.97 (s, 1H), 8.32 (d, J = 7.5 Hz, 2H); $^{13}$C NMR (75.5 MHz, $CDCl_3$) δ 4.5, 6.5, 13.6, 23.3, 25.4, 35.4, 35.7, 55.1, 58.4, 72.8, 79.8, 86.6, 87.0, 89.6, 94.4, 111.2, 113.1, 113.1, 127.0, 127.9, 128.0, 129.7, 129.9, 130.0, 132.3, 135.2, 135.3, 136.1, 137.0, 144.3, 147.4, 158.6, 159.7, 179.4; HRMS (MALDI) Calculated for $C_{49}H_{57}N_3O_8NaSi$ $[M + Na]^+$: 866.3813, Found 838.3809. |

(2-4) Synthesis of Compound 19

[Chemical Formula 36]

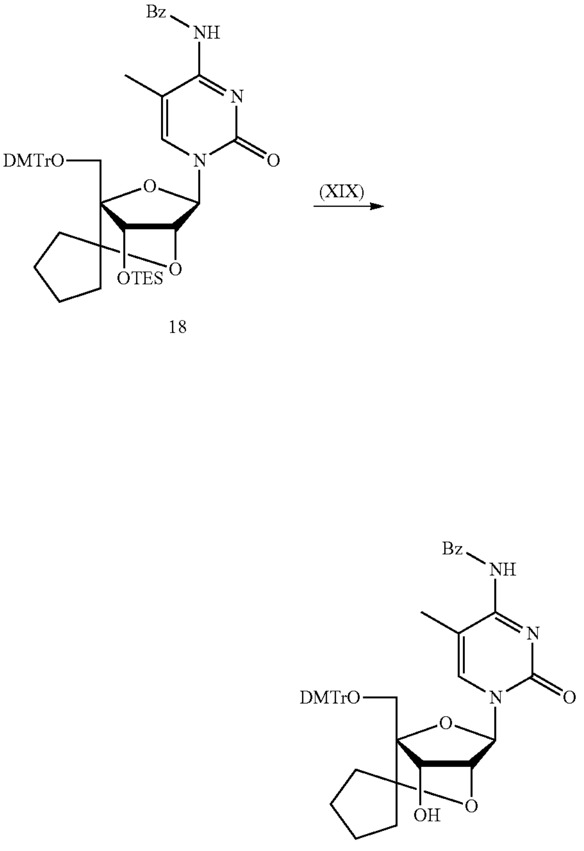

18

19

A 1 M tetrabutylammonium fluoride/tetrahydrofuran solution (120 μL, 120 μmol), was added at 0° C. to a tetrahydrofuran solution (1.2 mL) of the compound 18 (108 mg, 121 μmol) obtained above, and the resulting mixture was stirred at room temperature for 20 minutes. After completion of the reaction, the solvent was distilled away under reduced pressure. The obtained crude product was purified through silica gel column chromatography ($SiO_2$, chloroform:methanol=20:1) to obtain a compound 19 (101 mg, quantitative) as a white foam-like solid.

Table 15 shows data on the properties of the obtained compound 19.

TABLE 15

| Physical property data of the obtained compound 19 |
|---|
| $^1$H NMR (300 MHz, $CDCl_3$) δ 1.25-1.34 (m, 1H), 1.60-2.06 (m, 7H), 1.89 (s, 3H), 3.55 (s, 2H) 3.82 (s, 6H), 4.30 (d, J = 7.2 Hz, 1H), 4.40 (s, 1H), 5.61 (s, 1H), 6.88 (d, J = 8.9 Hz, 4H), 7.24-7.56 (m, 12H), 7.85 (s, 1H), 8.32 (d, J = 7.2 Hz, 2H); $^{13}$C NMR (75.5 MHz, $CDCl_3$) δ 13.5, 23.3, 25.6, 35.6, 35.8, 55.1, 58.5, 72.6, 79.8, 86.5, 86.8, 89.6, 94.1, 111.2, 113.2, 127.0, 127.9, 129.7, 129.9, 132.4, 135.3, 135.3, 136.2, 136.8, 144.4, 147.5, 158.5, 159.7, 179.4; HRMS (MALDI) Calculated for $C_{43}H_{43}N_3O_8Na$ [M + Na]$^+$: 752.2948, Found724.2939. |

(2-5) Synthesis of Compound 20

[Chemical Formula 37]

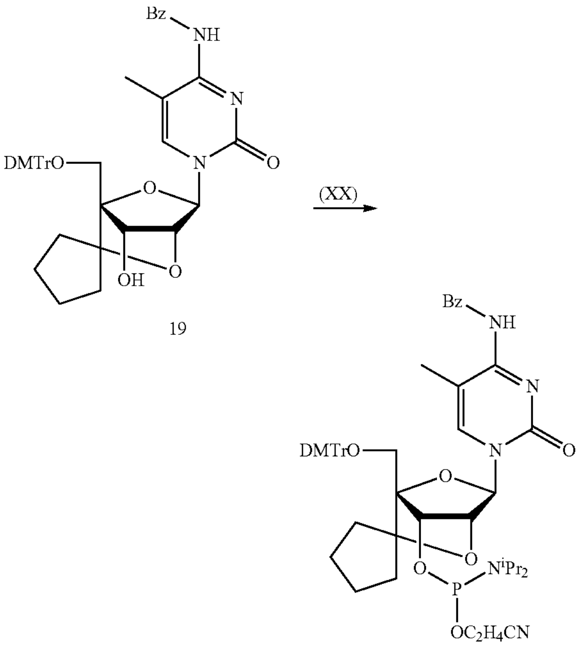

19

20

Under a nitrogen stream, 2-cyanoethyl N,N,N',N'-tetraisopropylphosphodiamidite (95 μL, 295 μmol) and 4,5-dicyanoimidazole (35 mg, 290 μmol) were added at 0° C. to an anhydrous acetonitrile solution (980 μL) of the compound 19 (71 mg, 97.3 μmol) obtained above, and the resulting mixture was stirred at room temperature for 2 hours. After completion of the reaction, the solvent was distilled away under reduced pressure. The obtained crude product was purified through silica gel column chromatography ($SiO_2$, 1% triethylamine-containing n-hexane:ethyl acetate=3:1) to obtain a compound 20 (73 mg, 81%) as a white foam-like solid.

Table 16 shows data on the properties of the obtained compound 20.

TABLE 16

| Physical property data of the obtained compound 20 |
|---|
| $^1$H NMR (500 MHz, $CDCl_3$) δ 0.98 (d, J = 6.9 Hz, 2H), 1.07 (d, J = 6.3 Hz, 4H), 1.12 (d, J = 6.9 Hz, 2H), 1.15 (d, J = 6.9 Hz, 4H), 1.26-2.05 (m, 8H), 1.77 (s, 2H), 1.83 (s, 1H), 2.34-2.37 (m, 3/2H), 2.51-2.63 (m, 1/2H), 3.47-3.56 (m, 6H), 3.81 (s, 2H), 3.82 (s, 4H), 4.38 (d, J = 7.4 Hz, 1/4H), 4.42 (d, J = 9.2 Hz, 3/4H), 4.56 (s, 3/4H), 4.58 (s, 1/4H), 5.63 (s, 1H), 6.84-6.89 (m, 4H), 7.28-7.52 (m, 12H), 7.89 (s, 1/4H), 7.91 (s, 3/4H), 8.31 (d, J = 7.5 Hz, 2H); $^{31}$P NMR (161.8 MHz, $CDCl_3$) δ 148.9, 149.4; HRMS (MALDI) Calculated for $C_{52}H_{60}N_5O_9NaP$ [M + Na]$^+$: 952.4021, Found 952.4005. |

(Example 3) Synthesis and Purification of Oligonucleotide (1)

An oligonucleotide was synthesized in the following manner using the compound 15 (scpBNA2nd-T) produced in Example 1 as an amidite block. Compounds other than the compound 15 constituting the oligonucleotide were purchased from Proligo unless otherwise stated. The following oligonucleotides were synthesized.

```
ON1:
                                  (SEQ ID No. 1)
5'-d(GCGTTYTTTGCT)-3'

ON2:
                                  (SEQ ID No. 2)
5'-d(GCGYTYTYTGCT)-3'

ON3:
                                  (SEQ ID No. 3)
5'-d(GCGTYYYYTGCT)-3'

ON4:
                                  (SEQ ID No. 4)
5'-d(GCGYYYYYYGCT)-3'

ON5:
5'-d(TTTTTTTTTY)-3'

ON6:
5'-d(TTTTTTTTYT)-3'
```

Y=Compound 15 (scpBNA2nd-T)

A 0.1 M anhydrous acetonitrile solution or a 0.1 M anhydrous dichloromethane solution was prepared using the compound 15 produced in Example 1 and fed into nS-8 Oligonucleotides Synthesizer manufactured by GeneDesign, Inc. Oligo synthesis was performed trityl-on. Activator-42 (registered trademark) (manufactured by Proligo) (0.25 M acetonitrile solution) was used as an activator, and the condensation time was extended to 150 seconds×5 for the compound 15. Regarding other operations, the synthesis was performed according to an ordinary phosphoramidite method.

After completion of the synthesis, the product was treated with a 28% aqueous solution of ammonia at room temperature for 1.5 hours, thus cleaved from the column support, and subsequently allowed to stand at 55° C. for 10 hours to thereby deprotect the base moiety. Then, the oligonucleotide was purified on a simplified reverse-phase column (Sep-Pak (registered trademark) Plus C18 Cartridges manufactured by Waters) and further purified by reverse-phase HPLC.

The composition of the purified oligonucleotide was determined by MALDI-TOF-MS. For this measurement, first, a matrix (1 μL) obtained by mixing an aqueous solution of 3-hydroxypicolinic acid (10 mg/mL) and an aqueous solution of diammonium citrate (1 mg/mL) in a volume ratio of 1:1 was dried on an AnchorChip. An aqueous solution of oligonucleotide (50 μM, 1 μL) was placed on the AnchorChip and then dried again. After that, MALDI-TOF-MS was performed. The molecular weight was measured in a negative mode, and oligothymidylic acids (7-mer, 9-mer, 11-mer, and 13-mer) were used as external standards. Also, the synthesized oligonucleotide was quantified by measuring ultraviolet absorption at 260 nm using an absorbance measurement apparatus (SHIMADZU UV-1800 manufactured by Shimadzu Corporation).

Table 17 below shows the results thereof.

TABLE 17

| ID | Oligonucleotide Sequence | Yield (%) | MALDI-TOF-MS (Mw.) Calculated $[M-H]^-$ | Found $[M-H]^-$ |
|---|---|---|---|---|
| ON1 | 5'-d(GCGTTYTTTGCT)-3' | 36 | 3714.5 | 3714.6 |
| ON2 | 5'-d(GCGYTYTYTGCT)-3' | 50 | 3878.7 | 3879.4 |

TABLE 17-continued

| ID | Oligonucleotide Sequence | Yield (%) | MALDI-TOF-MS (Mw.) Calculated $[M-H]^-$ | Found $[M-H]^-$ |
|---|---|---|---|---|
| ON3 | 5'-d(GCGTYYYTTGCT)-3' | 29 | 3878.7 | 3879.1 |
| ON4 | 5'-d(GCGYYYYYYGCT)-3' | 17 | 4125.0 | 4125.2 |
| ON5 | 5'-d(TTTTTTTTTY)-3' | 19 | 3061.1 | 3060.5 |
| ON6 | 5'-d(TTTTTTTTYT)-3' | 38 | 3061.1 | 3060.7 |

(Example 4) Assessment of Double-Strand Forming Ability

The double-strand forming ability of ON1 to ON4 was examined. 5'-d(GCGTTTTTTGCT)-3' ("ON9":SEQ ID No. 5) in which native DNA was used was also used as a control. A single-stranded oligo RNA 5'-r(AGCAAAAAACGC)-3' (SEQ ID No. 6) and a single-stranded oligo DNA 5'-d (AGCAAAAAACGC)-3' (SEQ ID No. 7) were used as target strands.

The double-strand forming ability of the oligonucleotides was examined by subjecting the different types of oligonucleotides and the target strands to an annealing treatment to form double strands, and then measuring their $T_m$ values. More specifically, a mixed liquid of each oligonucleotide (final concentration: 4 μM) and a phosphate buffer (10 mM, pH 7.2, 130 μL) containing sodium chloride (final concentration: 100 mM) was bathed in boiled water and then slowly cooled to room temperature. After that, the mixed liquid was cooled to 5° C. under a nitrogen stream before starting the measurement. The temperature was raised to 90° C. or 110° C. at a rate of 0.5° C./min while absorbance at 260 nm was plotted at intervals of 0.5° C. The $T_m$ value was calculated using a median method, and a mean value of three independent measurements was adopted.

Table 18 below shows the results. In Table 18, the results with respect to the single-stranded oligo-RNA are indicated by "ssRNA", the results with respect to the single-stranded oligo-DNA are indicated by "ssDNA", and the $T_m$ temperature change ("$\Delta T_m$/mod.") per artificially modified nucleic acid base of each oligonucleotide, and the RNA selectivity (the difference between the melting temperature for RNA and the melting temperature for DNA) are shown.

TABLE 18

| Oligonucleotide Sequence | | $T_m$[$\Delta T_m$/mod. = $T_m$[Modified] − $T_m$(Native](° C.)] | | RNA Selectivity |
|---|---|---|---|---|
| ID | 5'-ON-3' | ssDNA | ssRNA | $T_m$(RNA) − $T_m$(DNA) (° C.) |
| ON9 | GCGTTTTTTGCT | 51 | 47 | −4 |
| ON1 | GCGTTYTTTGCT | 52 (+1.0) | 53 (+6.0) | +1 |
| ON2 | GCGYTYTYTGCT | 55 (+1.3) | 63 (+5.3) | +8 |
| ON3 | GCGTYYYTTGCT | 53 (+0.7) | 62 (+5.0) | +9 |
| ON4 | GCGYYYYYYGCT | 82 (+1.8) | 79 (+5.3) | +17 |

When the compound 15 was used, both the single-stranded oligo DNA and the single-stranded oligo RNA exhibited higher melting temperatures than that of the native oligonucleotide (ON9). Furthermore, when the compound 15 was used, in particular, for the single-stranded oligo RNA, the $T_m$ value increased compared with that of the native oligonucleotide (ON9), which shows high binding affinity for the single-stranded oligo RNA. Also, when the compound 15 was used, RNA selectivity was confirmed.

(Example 5) Assessment of Nuclease-Resistant Ability

ON5 and oligonucleotides having the following 10-mer sequences were synthesized and purified, and the resulting oligonucleotides were used as test oligonucleotides.

5'-d(TTTTTTTTTX)-3'

(1) X=Compound 15 (ON5: "scpBNA2nd-T")
(2) X=phosphorothioate thymidine ("PS-T": for phosphorothioation, 0.05 M ((dimethylamino-methylidene) amino)-3H-1,2,4-dithiazolin-3-thione (DDTT) (pyridine/acetonitrile (3:2) solution, GLEN RESEARCH) was used.)
(3) X=spirocyclopropylene BNA (Patent Document 1 and Non-Patent Document 5: "scpBNA-T")

To a 50 mM tris-hydrochloric acid buffer (pH 8.0) containing 7.5 μM test oligonucleotide and 10 mM magnesium chloride was added 3'-exonuclease (Crotalus adamanteus venom phosphodiesterase, CAVP) with a concentration of 1.5 μg/mL, and the mixture was incubated at 37° C. At the start of the incubation (0 minutes) and 2.5, 5, 10, 20, and 40 minutes after the start of the incubation, a 20-μL aliquot was taken from the specimen and analyzed by reverse-phase HPLC to calculate the percentages of uncleaved oligonucleotides. Moreover, the assessment was derived from three independent measurements.

FIG. 1 shows the results thereof. In FIG. 1, solid-black rhombuses indicate the results with respect to the sequence (1) above, solid-black circles indicate the results with respect to the sequence (2) above, and solid-black triangles indicate the results with respect to the sequence (3) above. As is clear from FIG. 1, the oligonucleotide (sequence (1) above) having the compound 15 was not readily degraded, with approximately 70% remaining uncleaved even at 40 minutes after the nuclease treatment. It was found that the oligonucleotide (sequence (1) above) having the compound 15 had a very high level of nuclease resistance than the phosphorothioated (PS) oligo (sequence (2) above) and the oligonucleotide having spirocyclopropylene BNA (sequence (3) above).

(Example 6) Synthesis and Purification of Oligonucleotide (2)

Oligonucleotides shown in Table 19 were synthesized in the same manner as in Example 3 using the compound 15 (scpBNA2nd-T) produced in Example 1 and the compound 20 (scpBNA2nd-$^{Me}$C) produced in Example 2 as amidite blocks. Note that, with regard to phosphorothioation, 0.05 M ((dimethylamino-methylidene)amino)-3H-1,2,4-diazolin-3-thione (DDTT) (pyridine/acetonitrile (3:2) solution, GLEN RESEARCH) was used. The sequences of ONs21, ONs22, ONs23, and ONd1, which were the obtained oligonucleotides, are also respectively shown by SEQ ID Nos. 8 to 11.

TABLE 19

| ID | Sequence (5'-3') | Yields | Calculated [M − H]$^-$ | Found [M − H]$^-$ |
|---|---|---|---|---|
| ONs21 | $^{Me}$C^T^A^g^t^t^c^a^c^t^g^a^a^T^G^$^{Me}$C | 11% | 5504.7 | 5504.8 |
| ONs22 | $^{Me}$CTA^g^t^t^c^a^c^t^g^a^aTG$^{Me}$C | 25% | 5424.8 | 5425.9 |
| ONs23 | $^{Me}$CTA^g^t^t^c^a^c^t^g^a^a^TG^$^{Me}$C | 15% | 5456.8 | 5457.0 |
| ONd1 | G^T^T^a^t^g^c^c^a^c^c^$^{Me}$C^T^A | 19% | 4747.1 | 4747.1 |

Capital Letters = 2', 4'-BNA/LNA,
Underline Capital Letters = scpBNA-2nd,
Small Letters = DNA,
^ = Posphorothioated (PS)

(Example 7) Assessment of Toxicity Reduction Effect

The test oligonucleotides (20 mg/kg) shown in Table 20 were administered intraperitoneally to six-week-old mice (C57BL/6J, male) (5 mice/group). After 96 hours, blood was collected under inhalation anesthesia (isoflurane), and the mice were exsanguinated. Then, the activities of aspartate transaminase (AST) and alanine transaminase (ALT) in serum were measured using an automated analyzer (FUJI DRI-CHEM 4000V manufactured by FUJIFILM).

Note that, with regard to the test oligonucleotides shown in Table 20, ONd1 (SEQ ID No. 11) was produced in the same manner as in Example 6 using the compound 15 (scpBNA2nd-T) produced in Example 1 as an amidite block. ONd0 (SEQ ID No. 12) was produced in the same manner as ONd1, except that the compound 15 (scpBNA2nd-T) was not contained in the amidite block.

TABLE 20

| Test Oligonucleotide: | |
|---|---|
| ID | Sequence (5'-3') |
| ONd0 | G^T^T^a^t^g^c^c^a^c^c^$^{Me}$C^T^A |
| ONd1 | G^T^T^a^t^g^c^c^a^c^c^$^{Me}$C^T^A |

Capital Letters = 2', 4'-BNA/LNA,
Underlined Capital Letters = scpBNA-2nd,
Small Letters = DNA,
^ = Phosphorothioated (PS)

Table 21 shows the activities of aspartate transaminase (AST) and alanine transaminase (ALT) in blood in the cases where the test oligonucleotide was administered and in the case where a physiological saline solution was administered. In the group with administration of ONd0, which is known to exhibit hepatotoxicity, all of the five mice died. On the other hand, ONd1 in which a part of the sequence of ONd0 was substituted in the present invention showed almost no increase in ALT and AST, and thus the toxicity reduction effect was confirmed.

TABLE 21

| ID | ALT (IU/L) | AST (IU/L) | Remarks |
|---|---|---|---|
| Saline | 22.8 ± 1.6 | 73.8 ± 37.5 | — |
| ONd0 | — | — | All 5 died. |
| ONd1 | 73.2 ± 65.3 | 200.2 ± 160.9 | — |

ALT/AST Value: Means ± SD.

(Example 8) Assessment of Antisense Activity

With regard to the oligonucleotides (ONs21, ONs22, and ONs23: produced in Example 6) that contained the compound 15 (scpBNA2nd-T) produced in Example 1 and the compound 20 (scpBNA2nd-$^{Me}$C) produced in Example 2, and the oligonucleotide (ONs01) containing LNA instead of the compound 15 and the compound 20, the antisense activities in the tissues were examined.

The base sequences of these four oligonucleotides were designed as antisense nucleic acids for MALAT1. ONs01 was synthesized in the same manner as in Example 3, using LNA as an amidite block instead of the compound 15 and the compound 20. Table 22 below shows the sequences of ONs21, ONs22, ONs23, and ONs01.

TABLE 22

| ID | Sequence (5'-3') |
|---|---|
| ONs01 | $^{Me}$C^T^A^g^t^t^c^a^c^t^g^a^a^T^G$^{Me}$^C (SEQ ID No. 13) |
| ONs21 | $\underline{^{Me}\mathrm{C}}$^$\underline{\mathrm{T}}$^A^g^t^t^c^a^c^t^g^a^a^$\underline{\mathrm{T}}$^G^$\underline{^{Me}\mathrm{C}}$ (SEQ ID NO. 8) |
| ONs22 | $\underline{^{Me}\mathrm{CT}}$A^g^t^t^c^a^c^t^g^a^a$\underline{\mathrm{T}}$G$\underline{^{Me}\mathrm{C}}$ (SEQ ID No. 9) |
| ONs23 | $\underline{^{Me}\mathrm{CT}}$A^g^t^t^c^a^c^t^g^a^a^$\underline{\mathrm{T}}$G^$\underline{^{Me}\mathrm{C}}$ (SEQ ID No. 10) |

Capital Letters = 2', 4'-BNA/LNA,
Underlined Capital Letters = scpBNA-2nd,
Small Letters = DNA,
^ = Phosphorothioated (PS)

The test oligonucleotides (20 nmol: 200 μL of 100 μM physiological saline solution) were administered to the tail vein of six-week-old mice (BALB/cAnNCrlCrlj, female) (5 mice/group). After 72 hours, blood was collected under inhalation anesthesia (isoflurane), and the mice were exsanguinated. Then, the tissues were collected, and RNA extraction (kit used: RNeasy) was performed. The mRNA expression levels of MALAT1 in the tissues were measured by real-time PCR (kit used: One Step TB Green (registered trademark) PrimeScript™ RT-PCR Kit (Perfect Real Time), manufactured by Takara Bio Inc.). In the real-time PCR, the following primers were used.

```
MALAT1 forward:
                                        (SEQ ID No. 14)
acattccttgaggtcggcaa

MALAT1 reverse:
                                        (SEQ ID No. 15)
cacccgcaaaggcctacata

GAPDH forward:
                                        (SEQ ID No. 16)
tcaccaccatggagaaggc

GAPDH reverse:
                                        (SEQ ID NO. 17)
gctaagcagttggtggtgca
```

FIGS. 2 and 3 show the results thereof. FIGS. 2 and 3 show relative MALAT1 express levels in various tissues of mice in administration of various oligonucleotides (FIG. 2: liver, heart, kidney, pancreas, skeletal muscle, lung and stomach, and FIG. 3: spleen, skin, large intestine, brain, breast gland, eyeball, and cartilage). The "relative MALAT1 express levels" are shown as relative values in the case where the express level obtained when administration of only a physiological saline solution (no oligonucleotides) was taken as 1. In FIGS. 2 and 3, the bars showing the results are distinguished between the control (administration of only physiological saline solution), the oligonucleotide (ONs01) containing LNA instead of the compound 15 and the compound 20, and the oligonucleotides (ONs21, ONs22, and ONs23) containing the compound 15 and the compound 20.

The oligonucleotides (ONs21, ONs22, ONs23) containing the compound 15 and the compound 20 exhibited a target gene inhibitory effect that is equivalent to or better than that of the oligonucleotide (ONs01) containing LNA instead of the compound 15 and the compound 20 in many tissues.

INDUSTRIAL APPLICABILITY

According to the present invention, provided are a novel bridged nucleoside that is usable as a substitute for a phosphorothioate-modified nucleic acid, and a nucleotide using the bridged nucleoside. An oligonucleotide obtained using the bridged nucleoside of the present invention is useful as, for example, materials for oligonucleotide therapeutics.

The invention claimed is:

1. A compound represented by a formula (I-1) below or a salt thereof:

(I-1)

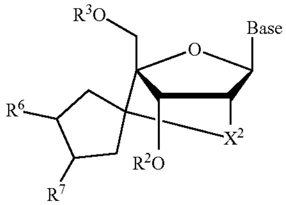

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, $R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms, $X^2$ is an oxygen atom, a sulfur atom, —NH—, —$N(CH_3)$—, or a methylene group, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms.

2. The compound or salt thereof according to claim 1, wherein the Base in the formula (I-1) is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

3. The compound or salt thereof according to claim 1, wherein the Base in the formula (I-1) is a group represented by a formula below:

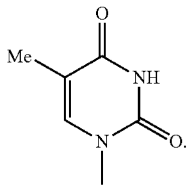

4. An oligonucleotide containing at least one nucleoside structure represented by a formula (II-1) below or a pharmacologically acceptable salt thereof:

(II-1)

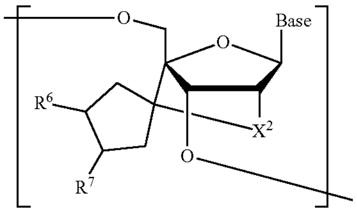

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms;

$X^2$ is an oxygen atom, a sulfur atom, —NH—, —$N(CH_3)$—, or a methylene group, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms.

5. A method for producing the oligonucleotide or pharmacologically acceptable salt thereof according to claim 4, comprising:

synthesizing an oligonucleotide using a compound represented by a formula (Ia) below or a pharmacologically acceptable salt thereof:

(I-1)

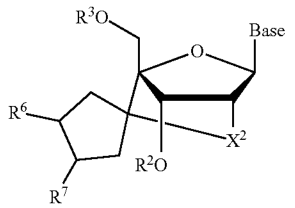

where Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, $R^2$ and $R^3$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 10 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α group, a phosphate group that may have any one or more substituents selected from the α group, a phosphate group protected by a protecting group for nucleic acid synthesis, or —$P(R^{4a})R^{5a}$, where $R^{4a}$ and $R^{5a}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 6 carbon atoms, an alkylthio group having 1 to 6 carbon atoms, a cyanoalkoxy group having 1 to 6 carbon atoms, or a dialkylamino group that has an alkyl group having 1 to 6 carbon atoms, $X^2$ is an oxygen atom, a sulfur atom, —NH—, —$N(CH_3)$—, or a methylene group, and $R^6$ and $R^7$ are each independently a hydrogen atom, a linear alkyl group having 1 to 3 carbon atoms, —$NHR^{4b}$, where $R^{4b}$ is a hydrogen atom or a linear alkyl group having 1 to 3 carbon atoms, or —$OR^{5b}$, where $R^{5b}$ is a hydrogen atom or a linear alkyl group having 1 to 3 carbon atoms.

6. The compound or salt thereof according to claim 1, wherein the Base in the formula (I-1) is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

7. The compound or salt thereof according to claim 1, wherein the Base in the formula (I-1) is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

8. The compound or salt thereof according to claim 1, wherein the Base in the formula (I-1) is a group represented by a formula below:

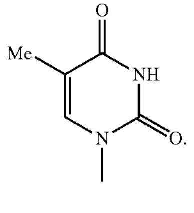

9. The compound or salt thereof according to claim 1, wherein the Base in the formula (I-1) is a group represented by a formula below:
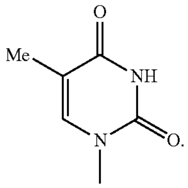
10. The compound or salt thereof according to claim 2, wherein the Base in the formula (I-1) is a group represented by a formula below:
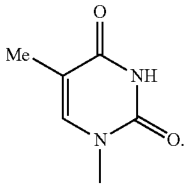
* * * * *